(12) United States Patent
Tranquillo et al.

(10) Patent No.: US 8,192,348 B2
(45) Date of Patent: Jun. 5, 2012

(54) ENGINEERED BLOOD VESSELS

(75) Inventors: Robert T. Tranquillo, Arden Hills, MN (US); Jeffrey Ross, Roseville, MN (US); Morayma Reyes, Sammamish, WA (US)

(73) Assignee: Regents of the University of Minnesota, Minneapolis, MN (US)

( * ) Notice: Subject to any disclaimer, the term of this patent is extended or adjusted under 35 U.S.C. 154(b) by 1030 days.

(21) Appl. No.: 10/562,955

(22) PCT Filed: Jul. 1, 2004

(86) PCT No.: PCT/US2004/021414
§ 371 (c)(1),
(2), (4) Date: Aug. 3, 2006

(87) PCT Pub. No.: WO2005/003317
PCT Pub. Date: Jan. 13, 2005

(65) Prior Publication Data
US 2007/0128171 A1 Jun. 7, 2007

Related U.S. Application Data

(60) Provisional application No. 60/484,563, filed on Jul. 1, 2003, provisional application No. 60/484,595, filed on Jul. 2, 2003.

(51) Int. Cl.
*A61F 2/04* (2006.01)
(52) U.S. Cl. .................. 600/36; 435/1.1; 435/284.1
(58) Field of Classification Search .................. None
See application file for complete search history.

(56) References Cited

U.S. PATENT DOCUMENTS

| | | | |
|---|---|---|---|
| 5,766,584 A | 6/1998 | Edelman et al. | |
| 5,792,603 A * | 8/1998 | Dunkelman et al. | 435/1.2 |
| 6,387,663 B1 * | 5/2002 | Hall et al. | 435/69.7 |
| 6,506,398 B1 * | 1/2003 | Tu et al. | 424/423 |
| 7,015,037 B1 | 3/2006 | Furcht et al. | |
| 2004/0107453 A1 | 6/2004 | Furcht et al. | |
| 2005/0181502 A1 | 8/2005 | Furcht et al. | |
| 2005/0283844 A1 | 12/2005 | Furcht et al. | |
| 2006/0008450 A1 | 1/2006 | Furcht et al. | |
| 2006/0030041 A1 | 2/2006 | Furcht et al. | |
| 2006/0177925 A1 | 8/2006 | Rosenberg et al. | |
| 2006/0228798 A1 | 10/2006 | Verfaillie et al. | |
| 2006/0263337 A1 | 11/2006 | Maziarz et al. | |
| 2007/0009500 A1 | 1/2007 | Blazar et al. | |
| 2007/0059823 A1 | 3/2007 | Verfaillie et al. | |
| 2008/0031820 A1 | 2/2008 | Verfaillie et al. | |
| 2008/0194021 A1 | 8/2008 | Mays | |
| 2008/0194024 A1 | 8/2008 | Mays | |
| 2008/0274088 A1 | 11/2008 | Blazar et al. | |
| 2008/0311084 A1 | 12/2008 | Verfaillie et al. | |
| 2008/0317740 A1 | 12/2008 | Blazar et al. | |

FOREIGN PATENT DOCUMENTS

| | | |
|---|---|---|
| WO | WO 08/063675 | 5/2008 |
| WO | PCT/IB08/003868 | 10/2008 |
| WO | PCT/US09/31528 | 1/2009 |

OTHER PUBLICATIONS

Niklason et al, "Functional Arteries Grown in Vitro" Science 1999, vol. 284, pp. 489-493.*
Henrikson RC, Kaye GI, and Mazurkiewicz JE (Eds.), Histology. Philadelphia: Lippincott Williams & Wilkins, 1997.*
Freshney, R Ian (Ed). Culture of Animal Cells: A manual of basic technique. (4th edition) New York: Wiley-Liss, 2002. p. 100.*
Shum-Tim et al, "Tissue Engineering of Autologous Aorta using a new biodegradable polymer" Ann Thorac Surg (1999) vol. 68: 2298-2305.*
Mitchell et al, "Requirements for Growing Tissue-Engineered Vascular Grafts" Cardiovascular Pathology (2003), vol. 12, pp. 59-64.*
Communication, submitted to USPTO on Oct. 2, 2007 for related U.S. Appl. No. 11/238,234.
Second Communication, submitted to USPTO on Dec. 24, 2008 for related U.S. Appl. No. 11/238,234.
International Search Report and Written Opinion, mailed May 16, 2006 for related PCT Application No. PCT/US04/21414.
Aldous et al., "Flawed stem cell data withdrawn" New Scientist; (Feb. 15, 2007).
Aldous et al., "Fresh questions on stem cell findings" New Scientist; (Mar. 24, 2007).
Check "Stem cell paper corrected" Nature; 447:763 (2007) and Jiang et al., "Pluripotency of mesenchymal stem cells derived from adult bone marrow" Erratum in Nature; 447:879.
Chi, "Adult stem cell figure retracted" The Scientist; (Jun. 13, 2007).
Giles, J., "The trouble with replication" Nature, 422:344-347 (2006).
Glenn, "Paper on versatility of adult stem cells comes under question" The Chronicle; (Feb. 26, 2007).
Holden, "Stem Cells. Controversial marrow cells coming into their own?" Science; 315:760-761 (2007).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Lerner et al., "Stem cell study was flawed, U panel finds" Star Tribune; (Feb. 27, 2007).
Noonan, "Limitations on the usefulness of adult stem cells" Patent Docs (Feb. 28, 2007).
Pincock, "Adult stem cell report questioned" The Scientist (Feb. 26, 2007).
Reyes et al., "Purification and ex vivo expansion of postnatal human marrow mesodermal progenitor cells" Blood; 98:2615-25 (2001).
Serafini et al., "Hematopoietic reconstitution by multipotent adult progenitor cells: precursors to long-term hematopoietic stem cell" J. Exp. Med.; 204:129-139 (2007).
Verfaille, "Multipotent Adult Progenitor Cells: an Update" Novartis Found Symp; 254:55-65 (2005).
Ratcliffe et al., "Tissue engineering of vascular grafts" Matrix Biology; 19:353-357 (2000).

(Continued)

*Primary Examiner* — Allison Ford
(74) *Attorney, Agent, or Firm* — Tarolli, Sundheim, Covell & Tummino LLP

(57) ABSTRACT

The present invention relates to engineered blood vessels and methods of making such vessels using matrices comprising endothelial and smooth muscle cells, or cells capable of differentiating into endothelial and smooth muscle cell lineages (e.g., stem cells, or the progenitors thereof).

10 Claims, 13 Drawing Sheets

OTHER PUBLICATIONS

Weinberger et al., "A blood vessel model constructed from collagen and cultured vascular cells" Science; 24:397-400 (1986).

L'Heureux et al., "In vitro construction of a human blood vessel from cultured vascular cells: a morphologic study" J Vasc Surg; 17:499-509 (1993).

Supplemental Information Disclosure Statement submitted to the USPTO in related U.S. Appl. No. 11/238,234, filed Oct. 4, 2007 and the accompanying Form 1449.

Public Statement from the University of Minnesota.

Tranquillo et al., "The tissue-engineered small-diameter artery" Ann NY Acad Sci; 961:251-254 (2002).

Jiang et al., "Pluripotency of mesenchymal stem cells derived from adult marrow, Supplemental Information for Verfaillie Corrigendum" Nature; 418:41-49 (2002).

Verfaillie, "Letter to the Editor" Experimental Hematology; (2007).

* cited by examiner

ENGINEERED BLOOD VESSELS

RELATED APPLICATIONS/PATENTS & INCORPORATION BY REFERENCE

This application claims priority to U.S. Application Ser. No. 60/484,563, filed Jul. 1, 2003, and U.S. Application Ser. No. 60/484,595 filed Jul. 2, 2003.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the numbered paragraphs, or in the text itself; and, each of these documents or references ("herein-cited references"), as well as each document or reference cited in each of the herein-cited references (including any manufacturer's specifications, instructions, etc.), is hereby expressly incorporated herein by reference. Reference is specifically made to International application nos. PCT/US00/21387, filed on Aug. 4, 2000 (published as WO 01/110011 on Feb. 15, 2001), and PCT/US02/04652, filed on Feb. 14, 2002 (published as WO 02/064748 on Aug. 22, 2002), the contents of which are incorporated herein by reference.

STATEMENT OF RIGHTS TO INVENTIONS MADE UNDER FEDERALLY SPONSORED RESEARCH

This work was supported by NHLBI Grant HL60495. The government may have certain rights to the invention.

FIELD OF THE INVENTION

The present invention relates to engineered blood vessels and methods of making such vessels using matrices comprising endothelial and smooth muscle cells, or cells capable of differentiating into endothelial and smooth muscle cell lineages (e.g., stem cells, or the progenitors of ECs or SMCs). Other aspects of the invention are described in or are obvious from the following disclosure, and are within the ambit of the invention.

BACKGROUND OF THE INVENTION

Surgical treatment of vascular disease has become common, creating the need for a readily available, small-diameter vascular graft. Many patients who are in need of bypass surgery do not possess sufficient veins to act as replacements for their diseased arteries. Such medical realities have propagated efforts to engineer biological replacements for such arteries. The characteristics proposed for an "ideal" engineered small diameter artery include the following: it should be biocompatible, that is, non-thrombogenic and non-immunogenic, be able to simulate the physical attributes of arteries, i.e. elasticity, contractility, compliance (viscoelasticity), adequate strength, physiological transport properties (i.e. appropriate permeability to solutes and cells), and be resistant to infection as well (Mayer, J. E. et al, 2001; Conte, M. S., 1998; Niklason, L. E., 1999; Nerem, R. M., 2000). All of these characteristics are associated with a confluent, non-activated endothelium. Moreover, these characteristics ultimately result in an acceptable wound healing response without fibrosis.

Weinberg and Bell pioneered the first attempt at building blood vessels by demonstrating the feasibility of creating an adventitia-like layer made from fibroblasts and collagen, a media-like layer made from smooth muscle cells ("SMCs") and collagen, and an intima-like endothelial cell ("EC") layer constructed into a tubular configuration. In order to withstand physiological pressures, these constructs required support sleeves made from Dacron™, a synthetic material (Weinberg, C. B. and Bell, E., 1986) having biocompatibility issues.

Other approaches are currently being investigated, several of which do not involve the use of synthetic materials. One such approach is acellular, based on implanting decellularized tissues treated to enhance biocompatibility, strength, and cell adhesion/invasion leading to cellularization with host cells (Huynh, T. et al, 1999). It has yet to be elucidated whether these acellular grafts will elicit an inflammatory response in humans, and whether they will develop the host EC layer. Badylak and coworkers also attempted to use an implanted noncellular construct consisting of a rolled small intestinal submucosa (SIS) as a small diameter vascular graft, which serves to recruit cells from surrounding host tissue (Badylak, S. et al, 1999). However, as with other acellular studies, this study suffered from a lack of non-thrombogenic EC lining on the lumen of the graft.

Other approaches involve implantation of constructs possessing some degree of cellularity. The most recent of these is based on the concept of "self-assembly" wherein SMCs are grown to overconfluence on tissue culture plastic in medium inducing high extracellular matrix (ECM) synthesis (L'Heureux, N. et al, 1998; L'Heureux, N. et al, 2001). This leads to sheets of "neo-tissue" which are subsequently processed into multi-layer tubular form resembling the medial layer. The tube is cultured to maturity over a time span of 8 weeks. During maturation, the cells assumed a circumferential orientation and produced large amounts of ECM. While these artificial vessels could withstand impressive pressure stress, displaying rupture strengths comparable to those of native human coronary arteries, when grafted into a dog transplant model, the vessels displayed a 50% thrombosis rate after one week of implantation. This may be attributed to xenograft rejection.

Other approaches rely on a polymeric scaffold. One is based on forming a tube of a synthetic biodegradable polyglycolic acid polymer mesh and then seeding aortic SMCs and culturing it for a period of time, relying on active cell invasion or an applied pulsatile force to achieve cellularity (Shinoka, T. et al, 1998; Niklason, L. E. et al, 1999; Shinoka, T. et al, 2001; Niklason, L. E. et al, 2001). The other is based on a tube of a biopolymer formed with and compacted by tissue cells, where an appropriately applied mechanical constraint to the compaction yields circumferential alignment of fibrils and cells characteristic of the arterial medial layer (L'Heureux, N. et al, 1993; Barocas, V. H. et al, 1998; Seliktar, D. et al, 2000). However, the constructs lacked burst strength.

There have been relatively few in vivo studies. One published in vivo study using the acellular approach (chemically cross-linked submucosal collagen from small intestine) reported 100% patency in rabbits out to 13 weeks with invasion and indications of organotypic organization of invading smooth muscle and ECs (Huynh, T. et al, 1999). One published in vivo study using the self-assembly approach was limited by use of xenogeneic cells; the absence of an endothelium (to avoid hyperacute rejection) yielded low patency over the week studied (L'Heureux, N. et al, 1998).

It is therefore desirable to meet all of the aforementioned criteria for generating an engineered artery. For example, high burst strength is often at the expense of a compliance mismatch, which can lead to intimal hyperplasia at the suture line (L'Heureux, N. et al, 1998). Conversely, constructs that possess physiological compliance, lack burst strength (Girton, T. S., et al, 2000).

SUMMARY OF THE INVENTION

In one aspect, the present invention relates to engineered blood vessels, intermediate compositions and pharmaceutical compositions containing the blood vessels.

In one embodiment, the present invention relates to a composition in vitro comprising ECs and SMCs incorporated in a matrix circumferentially positioned around a tubular support. Supports of the invention are permeable, allowing the movement of one or more mitogenic and attractant factors (in combination) or one or more mitoattractant factors within the support to the ECs, such that a bilayer is formed.

In another embodiment, the present invention relates to an engineered blood vessel comprising an intimal layer of ECs incorporated in a matrix and a medial layer of SMCs incorporated in a matrix, said layers being circumferentially positioned around a tubular support.

In yet another embodiment, the present invention relates to a pharmaceutical composition comprising an engineered blood vessel in a pharmaceutically acceptable carrier, said engineered vessel comprising an intimal layer of ECs incorporated in a matrix and a medial layer of SMCs incorporated in a matrix, said layers being circumferentially positioned around a tubular support.

In yet another embodiment, the present invention relates to compositions in vitro comprising ECs and SMCs incorporated in a matrix circumferentially positioned around a tubular support, wherein one or more mitogenic and attractant factors (in combination) or one or more mitoattractant factors capable of permeating the support are present within the support.

In yet another embodiment, the present invention relates to a composition in vitro comprising a matrix containing incorporated ECs and SMCs, said matrix containing said incorporated cells being circumferentially positioned around a tubular support, said support allowing movement of one or more mitogenic and attractant factors (in combination) or one or more mitoattractant factors across the support to said ECs, said composition comprising one or more mitogenic and attractant factors (in combination) or one or more mitoattractant factors within said support.

In yet another embodiment, the engineered blood vessels of the invention may optionally have an adventitial layer comprising fibroblasts.

In yet another embodiment, the engineered blood vessels of the invention may optionally have a basement membrane.

In another aspect, the present invention relates to methods of making engineered vessels using matrices comprising ECs and SMCs. Accordingly, in one embodiment, the present invention provides a method of producing an engineered blood vessel, said method comprising the steps of
 a. incorporating at least ECs and SMCs in a matrix;
 b. circumferentially positioning the matrix on the outer surface of a tubular support, wherein the support allows movement of mitoattractant, attractant, and mitogenic factors from within the support to said ECs; and
 c. allowing movement of one or more mitogenic and one or more attractant factors or one or more mitoattractant factors present within the support to said ECs.

By this method, a bilayer is formed, wherein the endothelium (intimal layer) forms around the support, and is surrounded by a medial layer comprising SMCs.

In one embodiment, the ECs and SMCs are derived from stem cells, or the progenitors thereof, capable of differentiating into these lineages, thereby providing a virtually unlimited source of cells. In one embodiment, the ECs and SMCs are differentiated prior to incorporation into the matrix. In another embodiment, the ECs and SMCs are differentiated in situ following incorporation into the matrix.

In yet another embodiment, the invention provides a method of culturing cells in a matrix, said method comprising the steps of
 a. combining ECs and SMCs in a matrix;
 b. growing ECs and SMCs in a matrix on the exterior surface of a tubular support, wherein the support allows movement of mitoattractant, attractant, and mitogenic factors from within the support to said ECs; and
 c. allowing movement of one or more mitogenic and one or more attractant factors or one or more mitoattractant factors present within the support to said ECs.

In a further aspect, the invention also contemplates providing a subject in need thereof with a blood vessel composition of the invention. Accordingly, in one embodiment, the present invention relates to a method for providing a vascular graft to a subject in need thereof comprising providing to the subject a composition comprising an intimal layer of ECs incorporated in a matrix and a medial layer of SMCs incorporated in a matrix, said layers being circumferentially positioned around a tubular support.

Other aspects of the invention are described in or are obvious from the following disclosure, and are within the ambit of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference, in which.

Elastin fiber staining is in black; the red stain shows the presence of collagen; blue/black dots correspond to nuclei; and yellow corresponds to other tissues.

Figure 4:
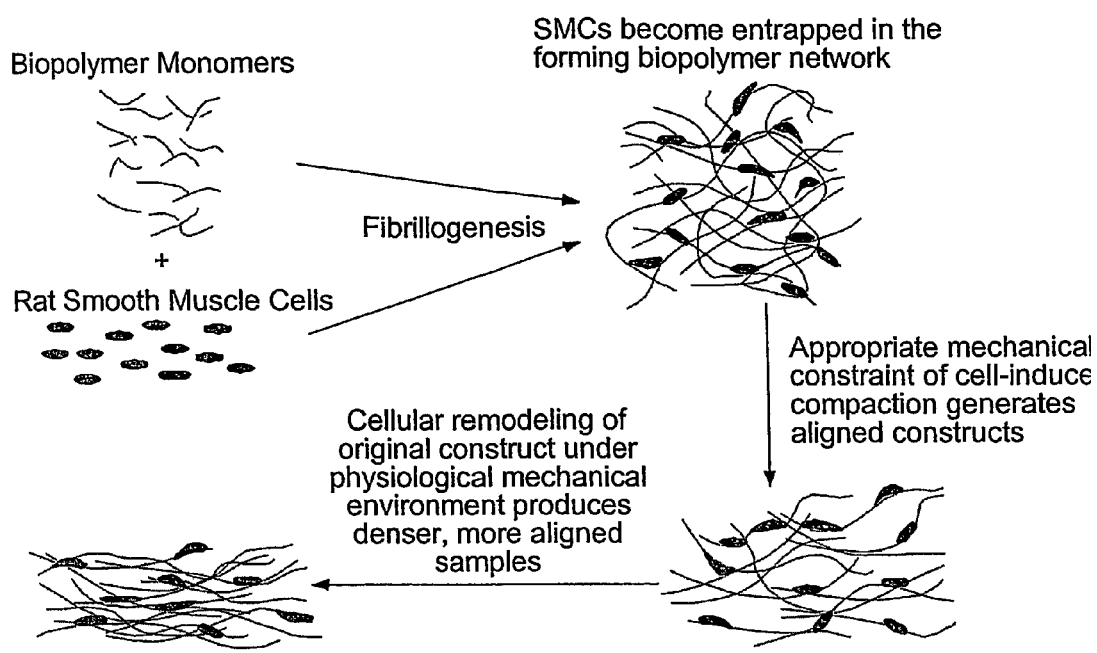
FIG. 4 shows a schematic overview of the organized tissue growth when rat SMCs are incorporated in a matrix.
Figure 5:
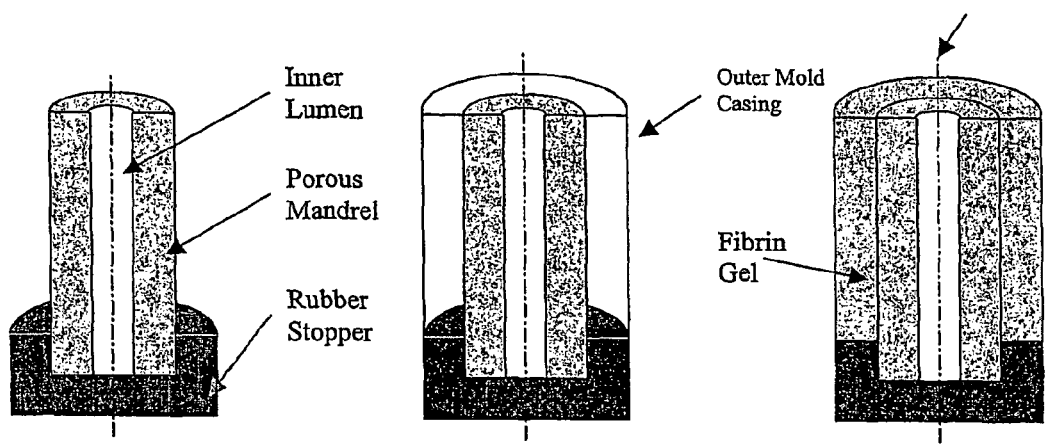
FIG. 5 shows a schematic of the formation of a tubular construct of fibrin gel around a porous tubular mandrel. ECs and SMCs of the present invention will attach along the interior surface. VEGF will circulate through the axial center of the tubular construct.
Figure 8:
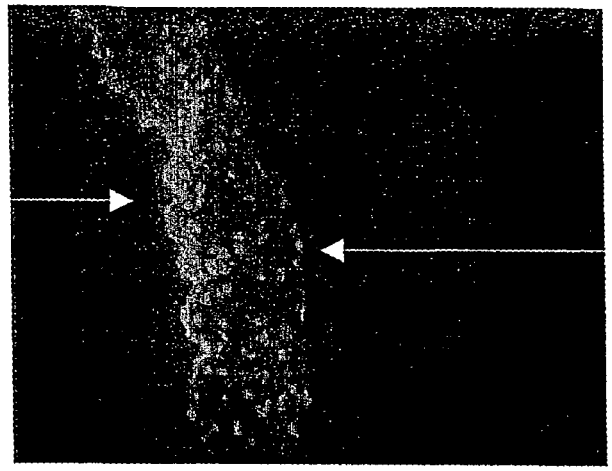

FIG. 8 shows an engineered blood vessel formed by the process in FIG. 4 with incorporation of neo-SMCs and MAPC-derived ECs using the method of FIG. 5. The micrograph depicts LDL uptake (left side of photo) relative to the plate surface (right side of photo).

Figure 9:
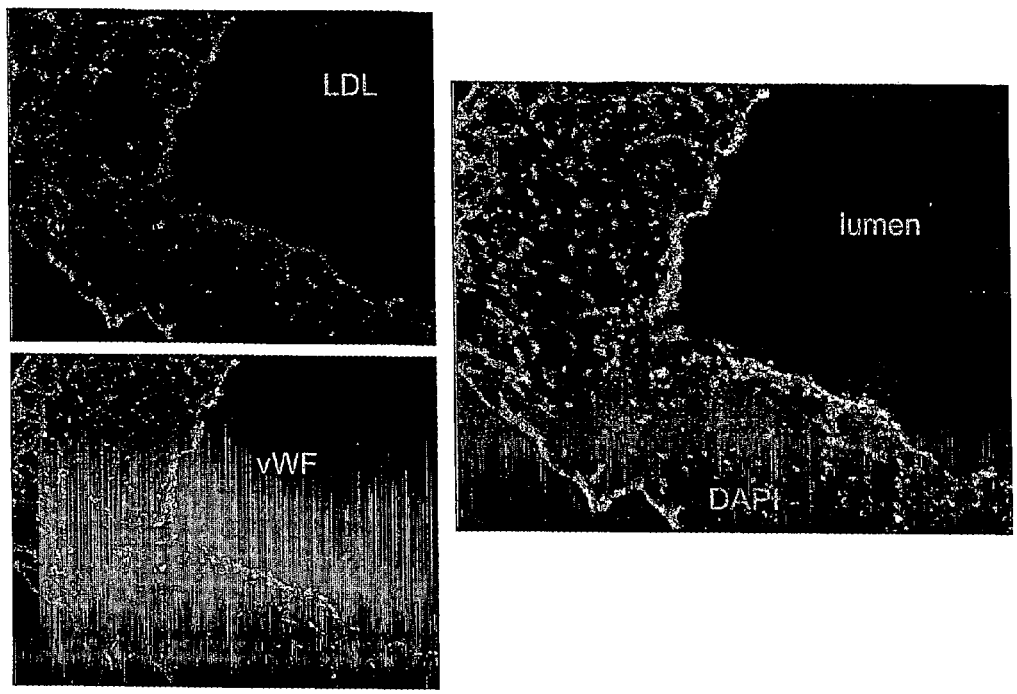

FIG. 9 shows a section of a vessel engineered by the methods of the invention after seven days in culture. LDL is shown in red; von Willebrand's Factor (vWF) is shown in green; and DAPI (nuclei) is shown in blue. Yellow indicates regions of overlap in LDL and vWF staining. ECs are mainly localized in the lumen after seven days of culture.

Figure 10:
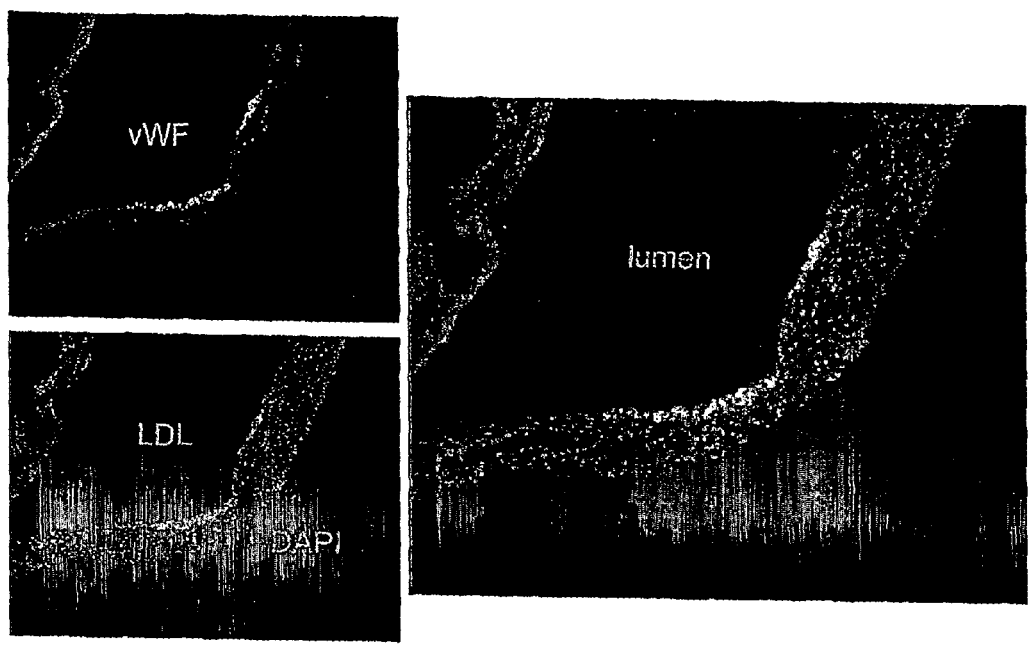

FIG. 10 shows a section of a vessel engineered by the methods of the invention after three weeks in culture. LDL is shown in red; von Willebrand's Factor (vWF) is shown in green; and DAPI (nuclei) is shown in blue. Yellow indicates regions of overlap in LDL and vWF staining. ECs are exclusively located in the lumen after three weeks of culture.

Figure 11A:
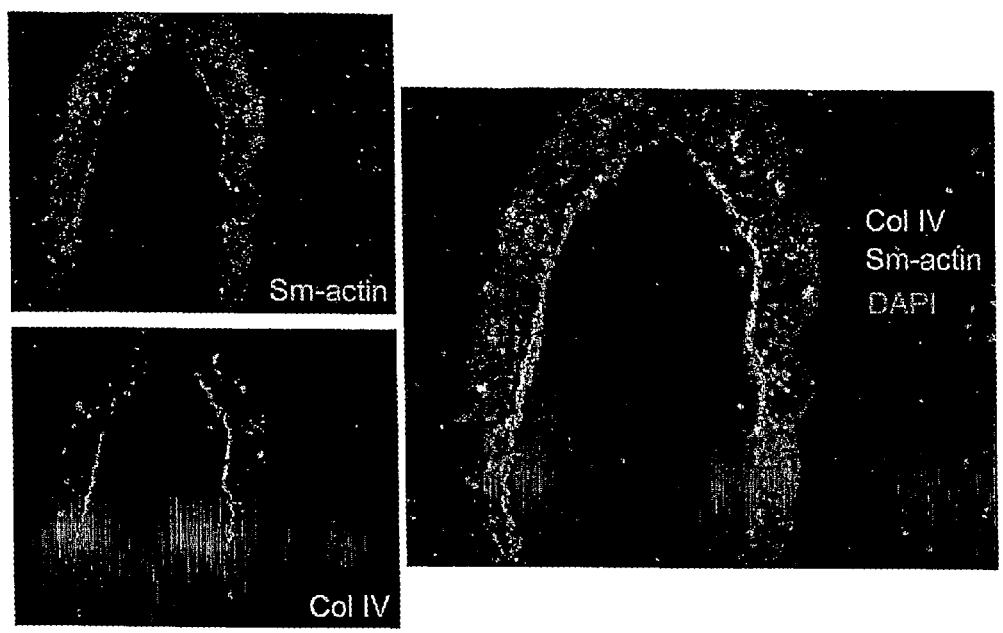
Figure 11B:
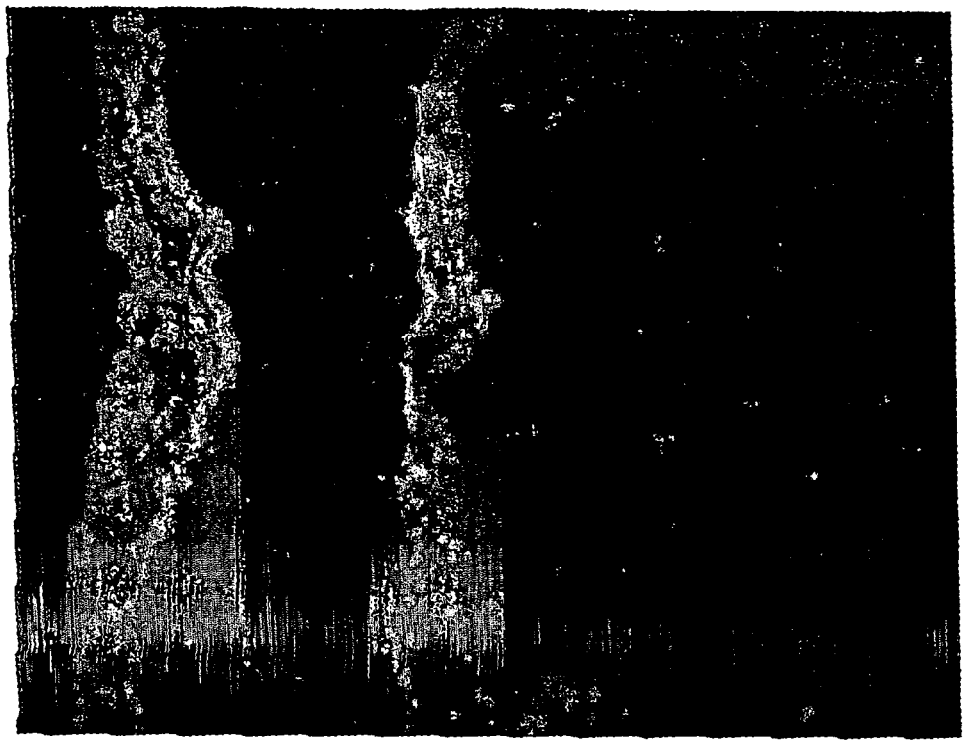
Figure 11C:
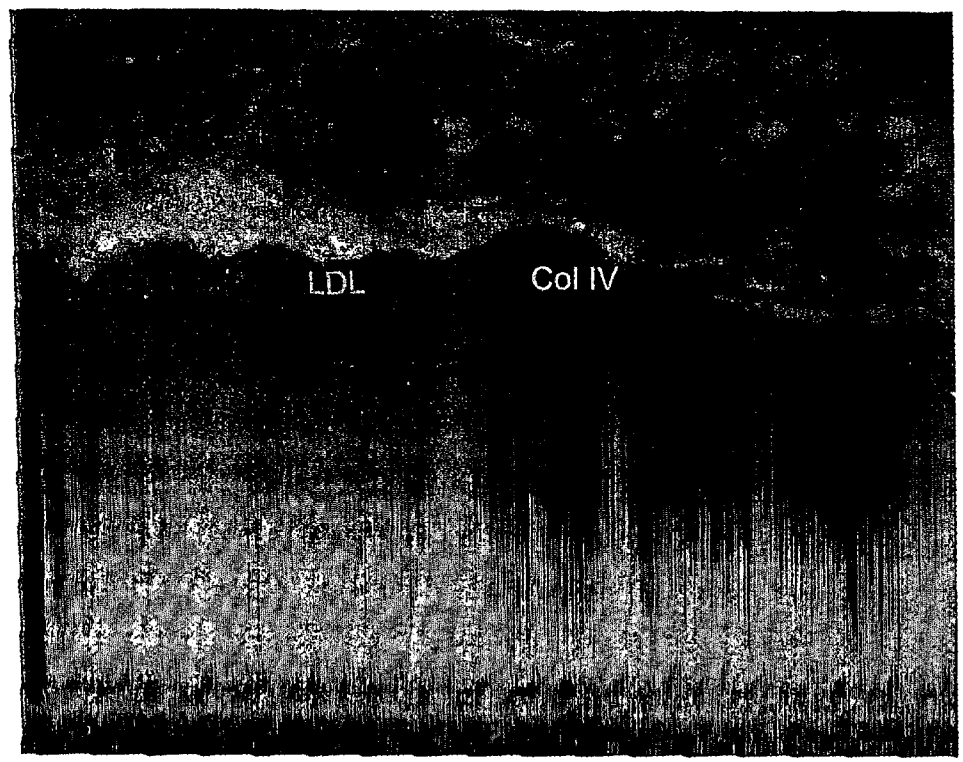

FIG. 11A shows a cross-section of the entire construct at lower magnification immunostained for α-smooth muscle-actin (red), collagen type IV (green), and DAPI (blue). FIGS. 11B and C show marked organization of the cellular layers, especially of a section near the lumenal surface of the construct after 5 weeks of incubation. The vessel was immunostained for LDL (red), collagen type IV (green), and DAPI (purple; stains nuclei).

DETAILED DESCRIPTION OF THE INVENTION

As used herein, the terms below are defined by the following meanings:

"Viscoelasticity" is a Theological parameter that describes the time-dependent deformation of a material. There are two components to the viscoelasticity: the viscosity and the elasticity. The viscosity is related to the energy dissipated during deformation and the elasticity is related to the energy stored during deformation.

"Vasoactivity" is the expanding and contracting of blood vessels to accommodate variations in blood flow, regulate arterial pressure, and meet the metabolic demands of the organs and body tissues.

An "endothelial cell" is a highly flattened cell type that forms the lining of all blood vessels and regulates exchanges between the bloodstream and surrounding tissues.

A "smooth muscle cell" is a type of muscle found in the walls of arteries and of the intestine and other viscera, which is composed of long, spindle-shapes mononucleate cells. SMCs lack the striations caused by the sarcomeres in skeletal and cardiac muscle cells.

A "bilayer" comprises an intimal layer of ECs circumferentially surrounded by a medial layer comprising SMCs. Layers may or may not be contiguous.

"Matrix" refers to any three-dimensional medium in which cells can be incorporated and, in response to the mitogenic, attractant or mitoattractant factor, become circumferentially aligned into a bilayer. In one embodiment, the matrix is contracted by the circumferential alignment of the cells.

"Support" describes a tubular structure that is permeable to mitogenic, attractant or mitoattractant factors of the invention (i.e., allows movement of one or more factors present within the support to move from the support to the ECs). In one embodiment, the support can be a porous support. The mitogenic, attractant or mitoattractant factor inside the support can be present in any medium that allows its movement through the support, for example, liquid, solid, and semi-solid mediums.

A "mitogenic" factor with respect to the invention is a biological or chemical factor that induces proliferation of ECs.

An "attractant" with respect to the invention is a biological or chemical factor that induces movement of ECs (e.g., by chemotaxis, where the factor is in a liquid gradient or by haplotaxis where the factor is bound to the matrix in a gradient). Such activity is believed to contribute to localization and alignment of ECs into an intimal layer of blood vessels of the invention.

A "mitoattractant" with respect to the invention is a biological or chemical factor having a combination of mitogenic and attractant activities for ECs.

In practicing methods of the invention, this combination of mitogenic and attractant activities can induce the formation of a bilayer from the admixture of ECs, SMCs and matrix.

"Vascular graft" refers to an engineered vessel of the invention, or a portion thereof.

"Stem cell" refers to a cell that can give rise to more than one cell type. Stem cells suitable for use in compositions and methods of the invention can give rise to a relevant cell type, including ECs, SMCs and/or fibroblasts. A "MAPC" is one type of stem cell. Another is an "embryonic stem cell."

"MAPC" is an acronym for a multipotent adult progenitor cell. It refers to a non-embryonic stem cell that can give rise to cell lineages of all three germ layers upon differentiation. See PCT/US00/21387, published as WO 01/11011, and filed as U.S. application Ser. No. 10/048,757 (specifically incorporated by reference for the description of MAPC isolation, characterization and preparation) and PCT/US02/04652, published as WO 02/064748, and filed as U.S. application Ser. No. 10/467,963 (specifically incorporated by reference for the description of MAPC isolation, characterization and preparation).

"Multipotent" refers to the ability to give rise to more than one differentiated cell type. MAPCs have extensive multipotency, in that they can give rise to cell lineages of all three germ layers (i.e., endoderm, mesoderm and ectoderm) upon differentiation.

"Germ layers" are the three primary layers formed as a result of gastrulation in early stage embryos, consisting of endoderm, mesoderm and ectoderm. Embryonic germ layers are the source from which all tissues and organs derive. The endoderm is the source of, for example, pharynx, esophagus, stomach, intestine and associated glands (e.g., salivary glands), liver, epithelial linings of respiratory passages and gastrointestinal tract, pancreas and lungs. The mesoderm is the source of, for example, smooth and striated muscle, connective tissue, vessels, the cardiovascular system, blood cells, bone marrow, skeleton, reproductive organs and excretory organs. Ectoderm is the source of, for example, epidermis (epidermal layer of the skin), sensory organs, the entire nervous system, including brain, spinal cord, and all the outlying components of the nervous system.

"Progenitor cells" are cells produced during differentiation of a stem cell that have some, but not all, of the characteristics of their terminally differentiated progeny. Defined progenitor cells are committed to a lineage, but not to a specific or terminally differentiated cell type. The term "progenitor" as used in the acronym "MAPC" does not limit these cells to a particular lineage.

"Endothelial progenitors" are progenitors that have committed to the endothelial cell lineage.

"Smooth muscle cell progenitors" are progenitors that have committed to the smooth muscle cell lineage.

"Heterologous cells" or "heterologous tissues" are allogeneic or xenogeneic, and are harvested from compatible donors. "Autologous cells" or "autologous tissues" are harvested from the individual in which the engineered vessel is to be implanted.

"Normal" refers to an animal or subject that is not diseased, mutated or malformed, i.e., healthy animals.

A "subject" is a vertebrate, preferably a mammal, more preferably a human. Subjects of the invention can be, but are not limited to unborn (e.g., a fetus or embryo) or newborn subjects. Mammals include, but are not limited to, humans, farm animals, sport animals, and pets.

The terms "comprises", "comprising", and the like can have the meaning ascribed to them in U.S. Patent Law and can mean "includes", "including" and the like.

Compositions and Methods of the Invention

Figure 1:
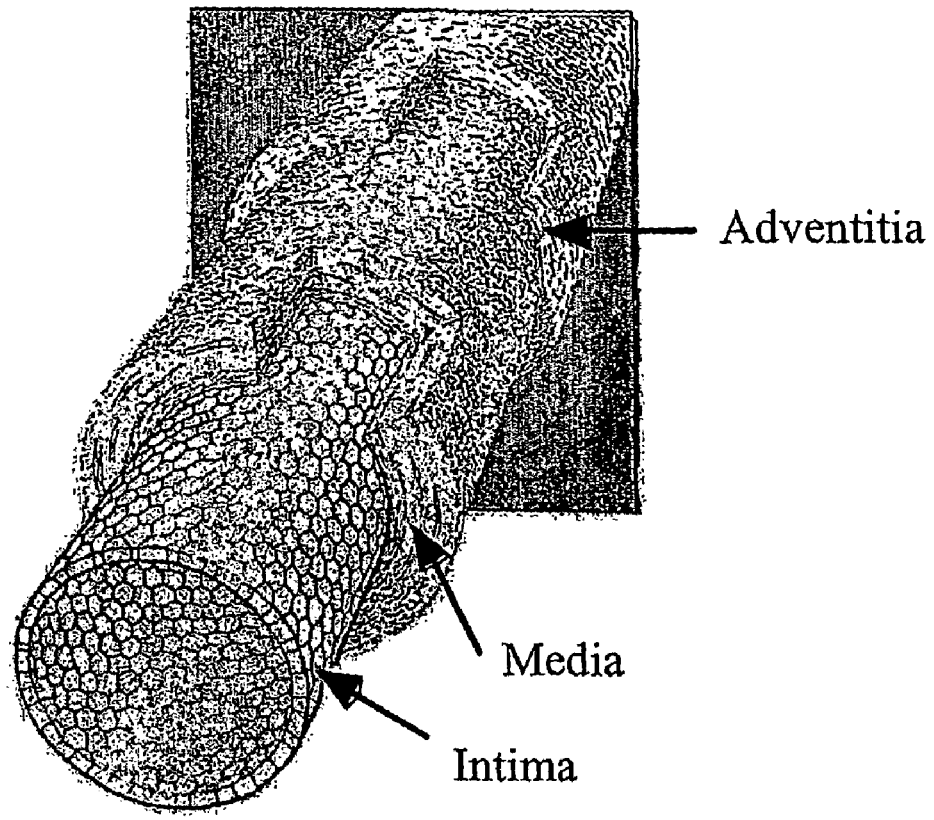
FIG. 1 shows the anatomy of an artery. An artery is comprised of three layers: adventitia, media, and intima, each made up of a distinct cell population.

The present invention provides engineered blood vessels and methods of making said vessels. Use of the term "engineered blood vessel" herein is intended to distinguish blood vessels of the invention from naturally occurring blood vessels. Naturally occurring blood vessels have a trilamellar structure, and each of the three layers confers specific functional properties on blood vessels (FIG. 1). The inner EC layer, or intima, is a single cell layer that prevents spontaneous blood clotting in the vessel and regulates vascular smooth muscle cell tone. The intimal layer is attached to a basement membrane, which is a thin layer of specialized ECM that can be readily identified by the presence of type IV collagen and laminin. The intermediate, or medial, layer is composed of SMCs and extracellular matrix components such as collagen, elastin, and proteoglycans. The medial layer contributes the bulk of the mechanical strength to the vessel as well as its native ability to contract or relax in response to external stimuli. The outer adventitial layer, composed primarily of fibroblasts and extracellular matrix, harbors the microscopic blood supply of the artery as well as its nerve supply.

Engineered compositions of the invention comprise ECs and SMCs incorporated in a matrix circumferentially positioned around a tubular support, wherein one or more mitogenic and attractant factors (in combination) or one or more mitoattractant factors capable of permeating the support are present within the support, and allowed to move from within the support to the ECs. Engineered blood vessels of the invention comprise an intimal layer of ECs and a medial layer of SMCs incorporated in the matrix and circumferentially positioned around the support.

The layers of the vascular tissue can be identified by any method known to the skilled artisan, such as immunostaining, immunoblotting, magnetic beads, flow cytometry, microarray analysis, or RT-PCR. The vascular tissue is preferably vasoactive and can be an artery or a vein.

Blood vessels of the invention are preferably vasoactive, implantable in a subject, and non-immunogenic to the subject in which it is implanted. Blood vessels of the invention can comprise vascular grafts, to be implanted into a subject to supplement or replace the biological function (e.g., structural, mechanical or metabolic activity) of a vascular tissue or organ (e.g., an artery). Engineered vessels of the invention can be implanted into patients by directly connecting the physiologic and engineered blood vessels to have continuous flow. Preferably, immediate perfusion of oxygenated blood occurs, which allows survival and function of the tissue.

Disease states in patients which may cause injury to the vasculature and thereby benefit from the implantation of a vascular graft include, but are not limited to, surgical procedures including bypass, congestive heart failure, coronary artery disease, myocardial infarction, myocardial ischemia, atherosclerosis, cardiomyopathy, cardiac arrhythmias, muscular dystrophies, muscle mass abnormalities, muscle degeneration, myasthenia gravis, infective myocarditis, drug- and toxin-induced muscle abnormalities, hypersensitivity myocarditis, autoimmune endocarditis, and congenital heart disease. In general, any disease or disorder which adversely affects the vasculature could be improved by methods of the invention that comprise providing engineered blood vessels to patients in need thereof.

The present invention further relates to methods of making engineered vessels. Thus, the present invention provides a method of producing an engineered blood vessel comprising incorporating at least ECs and SMCs in a matrix; and circumferentially positioning the matrix on the outer surface of a tubular support, wherein the support provides movement into the matrix of one or more mitogenic and attractant factors (in combination) or one or more mitoattractant factors present within the support, such that a bilayer is formed. Methods of the invention provide improved vessel structure, comprising an endothelium (intimal layer) formed around the support and surrounded by a medial layer comprising SMCs (i.e., a bilayer). In one embodiment, the matrix is comprised of a fibrillar material and during formation of the engineered vessel, the ECs and SMCs contract the matrix around the support, which promotes circumferential alignment of fibrils and cells.

I. Factors

Providing one or more mitogenic and attractant factors (in combination), or one or more mitoattractant factors (collectively referred to here in as "factors of the invention") further promotes physiological organization of the incorporated cells into the intimal and medial layers present in blood vessels in vivo. Such factors of the invention can be, but are not limited to FGF-1, FGF-2, FGF-4, angiogenin, angiopoietin, angiotensin, endothelin, AcSDKP (acetyl-N-Ser-Asp-Lys-Pro), Angiomodulin, Angiotropin, endothelial cell growth factor (ECGF), B61, endothelioma-derived motility factor, epidermal growth factor (EGF), endothelial cell-viability maintaining factor, IGF-1, heparin-binding neurotrophic factor (HBNF), human uterine angiogenesis factor (HUAF), platelet-derived endothelial cell growth factor (PD-ECGF), platelet-derived growth factor (PDGF), Placenta growth factor/vascular permeability factor, transferring, transforming growth factor-beta, interleukin-8, and growth hormone (GH).

Without being bound by theory, it is believed that the attractant and mitogenic activities of such factors promote segregation and expansion of ECs onto the luminal surface of the tube. In one embodiment, one or more mitoattractant factors having dual activity can be used. Alternatively, a combination of one or more mitogenic and attractant factors can be used together. In one embodiment, the mitoattractant factor of the invention is Vacsular Endothelial Growth Factor, or "VEGF." The invention therefore contemplates the use of angiogenic factors, when such factors have a desired effect on ECs.

Assays to be employed in assessing the mitogenic or attractant activity of a particular factor are known in the art. For example, assays to monitor cell movement in response to attractant factors are described in U.S. Pat. No. 6,448,054. Assays for identifying a mitogenic factor of the invention would be well-known and routine in the art. Mitogenic activity can be determined by detecting the proliferation of endothelial cells in vitro or in vivo. Assays for detecting endothelial cell proliferation would be known to the skilled artisan. Similarly, attractant factors can also be identified by in vitro assays to detect migration of endothelial cells. Cells may be placed in medium mimicking in vivo material so as to allow tactic gradients to form.

The concentration of factors used to form the bilayer is empirical and is based on such parameters as activity of the factor, density of the cells, density of the matrix, specific formulation of the matrix and distance to the cells and the like. Therefore such concentrations would be determined by routine experimentation.

II. Supports

Tubular supports of the invention are permeable, thereby allowing movement of factors of the invention from within the support to ECs in the matrix.

Pore size can vary based on the specific factors being used. Assays to determine the appropriate pore size can be done for example in vitro by partitioning the desired factor with a support and measuring diffusion to the other side of the support. In most instances, a diameter of about 70 microns will allow the passage of factors in the invention. However, a range of pore sizes tailored for each factor can vary (between about 10-20 microns, about 20-30 microns, about 30-40 microns, about 40-50 microns, about 50-60 microns, about 60-70 microns, about 70-80 microns, about 80-90 microns, and about 90-100 microns).

The diameter of the support will vary depending on the desired size of the vessel to be implanted. Similarly, the thickness of the support will vary depending on the specific physiologic function of the engineered blood vessel. In conjunction with the matrix, the thickness of the support is determined so that the physical attributes of the vessel (such as elasticity, contractility, strength and compliance) are achieved. Accordingly, as with diameter, the thickness of the support may vary depending on whether the vessel to be implanted approximates a coronary artery, for example, or a smaller blood vessel.

The support used to culture the cell-matrix composition is preferably comprised of porous material having a pore size large enough to allow passage of factors of the invention (e.g., about 70 μm). Preferably, the porous material is polyethylene, a polyethylene derivative, polycarbonate, polylactic acid (PLA), or polyglycolic acid (PGA).

Other materials suitable for fabrication of the support include, but are not limited to, poly-dimethyl-siloxane (PDMS), poly-glycerol-sebacate (PGS), poly-L-lactic acid (PLLA), poly-D-lactic acid (PDLA), polyglycolide, polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo(ε-caprolactone)diol as switching segment/oligo(p-dioxyanone)diol as physical crosslink. Other suitable polymers can be obtained by reference to The Polymer Handbook, 3rd edition (Wiley, N.Y., 1989). Combinations of these polymers may also be used.

PLGA, as well as PLA and PGA have been used to make biodegradable implants for drug delivery. See U.S. Pat. No. 6,183,781 and references cited therein. Biodegradable materials have been developed for use as implantable prostheses, as pastes, and as templates around which the body can regenerate various types of tissue. Polymers that are both biocompatible and resorbable in vivo are known in the art as alternatives to autogenic or allogenic substitutes.

External designs of the support can vary as well, for example, the support can be surrounded by an outer casing, enclosing the matrix, for example, as a mold, and providing an additional source of support for the cells within the matrix. The outer casing can be (but need not be) comprised of the same materials used to form the support.

In a specific embodiment, the support further is coated with agarose or some other permeable substance that renders it non-adhesive to the matrix.

In another specific embodiment, the system used to form a tubular fibrin gel for co-culturing cells can be comprised of a tubular porous polyethylene mandrel (e.g., 70 μm pore size), rubber stoppers, and optionally, an outer casing as shown in FIG. 5. Rubber stoppers can be placed on the ends of the porous mandrel. The mandrel with stoppers can be dipped into a 2% agarose solution to provide a nonstick surface on the outer surface of the polyethylene mandrel.

The coated mandrel with stoppers can optionally be placed into an outer casing made of plastic or glass. A needle can be inserted between the rubber stopper and the outer casing at one end to allow air to escape as the space is filled with solution. Once the matrix (e.g., fibrinogen solution and thrombin solution) and cell suspension are mixed, they can be injected between the outer casing and the porous mandrel using a needle and syringe. Preferably, the solution is allowed to gel at 37° C. in an incubator. A plunger can be used to gently push the rubber stoppers, porous mandrel, and fibrin gel out of the outer casing and into a container containing culture medium. See FIG. 4 for a schematic representation of one incorporation and organization process.

As the ECs and SMCs contract, the ends of the support can become exposed. Therefore, in one embodiment, the porous support comprises solid, or semisolid ends to prevent diffusion of the factor. Alternatively, the ends of the support may be closed with a sealant.

In one embodiment, medium comprising factors of the invention flows through the support. However, internal designs of the support can vary. For example, the support can be filled with any material (for example, liquid, solid, gel, or semisolid and the like) that allows the factors to reach the ECs. In one embodiment, the internal matrix or medium can facilitate the controlled or sustained release of factors of the invention.

III. Matrices

The matrix in which the ECs and SMCs are incorporated can be comprised of any suitable matrix material. Preferably the matrix is fibrillar (e.g., capable of forming fibrils), and comprised of, for example, fibrin, which is produced from the combination of fibrinogen and thrombin, collagen, fibronectin, amphiphilic di-block copolymers, or amphiphilic tri-block copolymers, or peptides (e.g., RGD peptides or amphiphilic peptides that can assemble into a fibrillar structure), but the invention is not so limited. Laminin, proteoglycans, Matrigel™ and other similar biomolecules provide suitable matrix materials. Preferably, the matrix is comprised of fibrin.

Matrigel™ is an example of a basement membrane matrix. Matrigel™ matrix is composed of laminin, collagen IV, nidogen/enactin, and proteoglycans. Other ECM-based gels, containing known components, can be used, such as collagen gels, laminin gels, and fibrin/fibrinogen gels. One embodiment of the present invention utilizes fibrin-based polymeric matrices, including the monomeric precursor, fibrinogen, in combination with thrombin to cleave fibrinogen into fibrinopeptides that self-assemble into fibrin fibrils ("fibrin").

Other matrices that are envisioned by the instant invention include amphiphilic block copolymers (Nardin, C. and Meier, W., 2002). These molecules consist of at least two parts with different solubilities, causing their self-assembly into superstructures in the sub-micrometer range, with cores consisting of their insoluble parts, surrounded by their soluble parts. This self-organization of block copolymers is based on the same underlying principles as for typical low molecular weight amphiphiles, such as surfactants or lipids in water. The high diversity of block copolymer chemistry allows for variation of the chemical constitution, the length and structure of different blocks, and the molecular architecture of the whole polymer. The equilibrium shape of amphiphilic aggregates is related to the molecular geometry of the underlying molecules. Manipulation of the shape and length of the hydrophilic blocks can cause a transition from spherical to worm-like micelles, and finally to vesicular structures. Such block copolymers include poly(ethyleneoxide)-poly(butadiene), or PEO-PB diblock copolymer, which forms giant worm-like micelles of dimensions similar to fibrin fibrils at low concentrations in water and exhibit viscoelastic properties in water (Won, Y. Y. et al, 1999) similar to a fibrin gel.

Other materials can include the siloxanes, such as poly [(aminopropyl)siloxane] (poly-APS) as a coupling agent to bond inorganic to organic materials. Poly-APS structures are attractive because they form extended oligomeric structures consisting of linear, cyclic, and cross-linked Si—O—Si polymeric networks. Additionally, poly-APS structures are amphiphilic, consisting of inorganic silanol and organic aminopropyl groups. Recent studies indicate that a poly-APS film doped with potassium ions forms a structure that self-assembles, has built-in error correction, forms well-defined fibrous structures, and in high-yields. Also, these microfibers can be easily disassembled by dissolution in an aqueous environment at room temperature (Celio, H. et al, 2003).

Cells can be incorporated into the matrix by routine methods of combining cells with any biocompatible substance. The cells, for example, may be present in any appropriate medium for retaining viability and function. It may be culture medium appropriate for ECs. Alternatively cells can be removed from culture by any appropriate physical or other means, for example by filtration or centrifugation, and then incorporated into the matrix.

The concentration of cells in the matrix can vary, depending on the thickness or length of the desired vessel. Generally, the concentration of ECs or SMCs (or stem cells or progenitor cells giving rise to the ECs or SMCs) is at least $10^6$ cells/ml matrix, but the invention is not so limited. Concentrations can range, for example, between $5 \times 10^5$, $5 \times 10^6$, $5 \times 10^7$, and $5 \times 10^8$ cells/ml matrix, however, concentrations lower than these ranges are also contemplated.

The thickness of the matrix material around the support can vary. Variability can be empirically determined by the size of the specific desired vessel to be implanted. The cell-matrix combination is then formed around the support and the resulting composition is cultured in the appropriate culture medium that allows the cells to remain viable. The matrix may be held in place or formed around the support by means of an outer casing that is circumferentially surrounding the support. In this case the culture medium can reach the cells from within the support, from open or otherwise permeable end(s) or by means of a casing that allows the medium to reach the cells.

The length of time that the composition is cultured to form the bilayer can vary depending on such parameters as factor concentration, factor activity, cell density, matrix compositions and the like. Accordingly, the length would be determined by routine assay for bilayer formation.

When stem or progenitor cells are incorporated in the matrix, appropriate differentiation factors are provided. Such differentiation factors can be provided in the matrix so that the SMCs and/or ECs are differentiated before, with, or after forming the matrix around the support. Alternatively or in addition, the differentiation factors can be provided externally, before, during, or after forming the matrix around the support. For example, the factors can be added to the cell-matrix combination in culture medium.

Cells of the Invention

Cells of the invention can be obtained by any method known in the art. Methods of obtaining the cells described herein are well known in the art, and can be performed as described here in or with variation, as a matter of routine practice. Alternatively, cells of the invention can be obtained from commercial suppliers, including VEC Technologies, Inc. and Clonetics, among others.

I. Endothelial Cells

ECs for use in methods and compositions of the invention can be of any kind, including, but not limited to, microvascular or large artery endothelium. ECs can be harvested from any vascular source. In one embodiment, the ECs (and/or the SMCs) are derived from vascular tissue, preferably pulmonary artery, pulmonary vein, femoral artery, femoral vein, saphenous artery, saphenous vein, iliac artery, iliac vein, umbilical artery, umbilical vein, microvascular tissue, adipose, placental, and aortic tissue. Microvascular tissue is preferably derived from heart, lung, liver, kidney, brain or dermal tissue, sinusoidal tissues and dermis-derived microvascular tissue sources.

Primary cell lines such as human microvascular endothelial cells (HMECs) and human umbilical vein endothelial cells (HUVECs) are commonly used sources for ECs, and grow well under certain conditions, in tissue culture. Vessel-derived ECs can be isolated by cannulation (i.e. "gut cleaners") and incubation of vascular tissues with collagenases or matrix metalloproteinases. Isolation of ECs are exemplified by work by Jaffe and coworkers (Jaffe, E. A., et al. 1973). The identity of ECs can be confirmed by their production of von Willebrand factor (vWF), and uptake of acylated low-density lipoprotein (acLDL).

II. Smooth Muscle Cells

SMCs also can be harvested from vascular sources, similar to ECs. A typical source, like ECs, is umbilical vein and artery, but can also include aorta, saphenous vein, femoral artery, iliac artery, iliac vein, pulmonary artery, and pulmonary vein, as well as heart, liver, lung, kidney, brain, and dermis-derived microvascular tissues. Harvesting and isolation of SMCs are described in Ross, 1971. SMCs can be advantageously identified by the presence of $\alpha$-actin, desmin, and smooth muscle myosin. Antibodies against these SMC-specific cellular markers are well known in the art and are commercially available.

In a specific embodiment, the isolation of neonatal SMCs can be carried out as described by Ross, (2003) and Diglio (1989). The aorta can be aseptically removed and placed in 1% penicillin/streptomycin (Gibco) in PBS (Mediatech). Fatty tissue surrounding the aorta and the adventitia are stripped away. The aorta is positioned longitudinally and scraped to remove the intima. The cleaned aorta is then cut into pieces and incubated in an enzyme solution consisting of 2.5 mg elastase and 10 mg collagenase (both from Sigma) in 20 ml DMEM for 1 hour at 37° C. After the incubation, the cells are pelleted, rinsed, and resuspended in DMEM supplemented with 10% fetal bovine serum (FBS) (Hyclone) and 1% penicillin-streptomycin. The cells are then seeded in 25 cm$^2$ plastic tissue culture flasks (Corning) with 5 ml of medium.

III. Fibroblasts

Fibroblasts can be harvested from bone marrow, lung, embryo, adipose tissue, subcutaneous connective tissue, areolar connective tissue, kidney, skin, and brain. Fibroblasts are precursors of many different types of connective tissue and can differentiate into osteoblasts of bone, adipocytes of fat, and chondrocytes in cartilage. Fibroblasts can be advantageously identified by the presence of prolyl-4-hydroxylase B and type I procollagen (Janin, A. et al, 1990). Fibroblasts can also be obtained by differentiation of stem cells such as MAPCs.

The cell sources can be autologous or heterologous to a subject who will receive the engineered blood vessel of the invention. For example, the present invention contemplates the use of autologous or isogeneic cells harvested from patients undergoing tissue grafting of the engineered blood vessels described herein. Preferably they are autologous and are non-immunogenic, such that an immune response is not elicited in a subject receiving a tissue-engineered blood vessel of the invention. As such, no immunosuppression is required prior to or following engraftment of the tissue-engineered blood vessel into a subject.

Another source of cells are those harvested from compatible donors (i.e., heterologous cells). It will be apparent to those skilled in the art that use of heterologous cells may require immunosuppression of the subject in need of a vascular graft to prevent rejection of foreign cells. Immunosuppression of the subject can be achieved using pharmacological agents such as, but not limited to, cyclosporine, tacrolimus, rapamycin, glucocorticoids such as prednisone and prednisolone, azathioprine, mycophenolate mofetil, methotrexate, cyclophosphamide, monoclonal antibodies such as muromonab-CD3, and anti-thymocyte globulin antibodies (Goodman and Gilman's *The Pharmacological Basis of Therapeutics*, 9$^{th}$ Edition).

IV. Stem Cells

One source of cells that can be used to derive ECs and SMCs are stem cells. In one embodiment of the invention, the stem cells are autologous, eliminating the need for immunosuppression.

In one embodiment, the ECs and/or the SMCs are derived from stem cells, or the progenitors thereof. The stem cells can be embryonic stem (ES) cells, embryonic germ (EG) cells, multipotent adult progenitor cells (MAPCs), mesenchymal stem cells (MSCs), and endothelial progenitor cells (EPCs). Most preferably, the stem cells are MAPCs. Stem cells can be derived from any appropriate tissue, and are preferably derived from bone marrow, brain, spinal cord, umbilical cord blood, liver, placenta, blood, adipose tissue, or muscle.

Stem cells that can be used in the present invention include MAPCs, or multipotent adult progenitor cells (Jiang, Y. et al, 2002). MAPCs derived from human, mouse, rat or other mammals appear to be the only normal, non-malignant, somatic cell (i.e., non-germ cell) known to date to express very high levels of telomerase even in late passage cells. The telomeres are extended in MAPCs and they are karyotypically normal. Because MAPCs injected into a mammal can migrate to and assimilate within multiple organs, MAPCs are self-renewing stem cells. As such, they have utility in the repopulation of organs, either in a self-renewing state or in a differentiated state compatible with the organ of interest. They have the capacity to replace cell types that could have been damaged, died, or otherwise might have an abnormal function because of genetic or acquired disease.

Human MAPCs are described in U.S. application Ser. No. 10/048,757 (see page 8, lines 23-32; p. 9, lines 1-22; p. 21, lines 19-32; p. 22, lines 1-27; p. 25, lines 20-31; pages 26 through p. 28, lines 1-13, 20-25; p. 29, lines 1-21) and U.S. application Ser. No. 10/467,963 (see p. 9, lines 29-32; p. 10, lines 1-25), specifically incorporated by reference for the characterization of MAPCs.

Methods of MAPC isolation are described in U.S. application Ser. No. 10/048,757 (p. 10, lines 17-32; p. 11, lines 1-12; p. 22, lines 29-32; p. 23, lines 1-32; p. 24, lines 1-28; p. 71, lines 28-32; p. 72 through p. 74, lines 1-27) and U.S. application Ser. No. 10/467,963 (p. 26, lines 13-34; p. 27 through p. 28, lines 1-27), specifically incorporated by reference for the methods of isolation described. Methods of MAPC culture are also described in U.S. application Ser. No. 10/048,757 (p. 23, lines 25-32) and U.S. application Ser. No. 10/467,963 (p. 26, lines 18-29), specifically incorporated by reference for the culture methods described.

Stem cells used in the present invention can also include embryonic stem cells (Lebkowski, J. S. et al, 2001). The quintessential stem cell is the embryonic stem (ES) cell, as it has unlimited self-renewal and pluripotent differentiation potential (Thomson, J. et al. 1995; Thomson, J. A. et al. 1998; Shamblott, M. et al. 1998; Williams, R. L. et al. 1988; Orkin, S. 1998; Reubinoff, B. E., et al. 2000). These cells are derived from the inner cell mass (ICM) of the pre-implantation blastocyst (Thomson, J. et al. 1995; Thomson, J. A. et al. 1998; Martin, G. R. 1981), or can be derived from the primordial germ cells from a post-implantation embryo (embryonal germ cells or EG cells). ES and/or EG cells have been derived from multiple species, including mouse, rat, rabbit, sheep, goat, pig and, more recently, from human and non-human primates (U.S. Pat. Nos. 5,843,780 and 6,200,806).

In one embodiment, stem cells for use in methods and compositions of the invention comprise hematopoietic stem cells (HSCs). It is thought that HSCs and endothelial progenitor cells (EPCs) arise from a common progenitor, known as the "hemangioblast" (Choi, K., 2002). These early precursors are thought to originate from the blood islands of the yolk sac during early development (embryonic day 7.5). Recent evidence indicates that a population of CD34-stem cells, which are potent HSCs that give rise to all blood cell lineages, are capable of contributing to regeneration of cardiac muscle and vascular endothelial cells (Jackson, K. A. et al, 2001). HSCs were able to repopulate vessel structures, demonstrating that these cells or their progeny had migrated to the injured heart via circulatory system, localized to newly forming vessels, and integrated into the surface lining as differentiated ECs (Jackson, K. A. et al, 2001).

Yet another stem cell for use in methods and compositions of the invention is the mesenchymal stem cell (MSC). Most, if not all, vessels develop from an endothelial tube that subsequently acquires a coating formed by vascular SMCs, which in turn develop from an undifferentiated perivascular mesenchymal progenitor (Hellstrom, M. et al, 1999). MSCs are thought to migrate out of the bone marrow into specific tissues, where they in turn differentiate into multiple lineages depending on the cellular microenvironment. MSCs can differentiate to form muscle, bone, cartilage, fat, marrow stroma, and tendon (Jiang, Y. et al, 2002). During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelial and hematopoietic progenitor cells. Primitive mesoderm or MSCs, therefore, could provide a source for a number of cell and tissue types, including ECs and SMCs. A number of MSCs have been isolated. (See, for example, Caplan, A., et al., U.S. Pat. No. 5,486,359; Young, H., et al., U.S. Pat. No. 5,827,735; Caplan, A., et al., U.S. Pat. No. 5,811,094; Bruder, S., et al., U.S. Pat. No. 5,736,396; Caplan, A., et al., U.S. Pat. No. 5,837,539; Masinovsky, B., U.S. Pat. No. 5,837,670; Pittenger, M., U.S. Pat. No. 5,827,740; Jaiswal, N., et al., 1997; Cassiede P., et al., 1996; Johnstone, B., et al., 1998; Yoo, et al., 1998; Gronthos, S., 1994).

Recent studies of the cells and genes expressed in the embryonic neural crests indicates similarities between neural crest and endothelial cell development (Gammill, L. S., and Bonner-Fraser, M., 2002). Eight genes isolated from a newly formed neural crest have been previously implicated in endothelial cell development, such as factors involved in VEGF production and signaling (ORP150 and neuropilin 2a1), as well as proteins important for EC migration, such as laminin α5 and γ1. In addition, one study demonstrated that multipotent neural stem cells can give rise to both ECs and SMCs. In another study, NSCs subcultured into collagen gel formed endothelial tube-like structures (Kawakita, E. et al, 2002). Therefore, neuronal stem cells can also be used in methods and compositions of the invention.

V. Endothelial Progenitor Cells

Endothelial progenitor cells (EPCs) are especially desirable for use in methods and compositions of the invention. EPCs are primarily responsible for differentiation into vascular tissues and can be found in peripheral blood and bone marrow, as well as sites of physiological and pathological neovascularization (Asahara, T. et al, 1997). As described above, EPCs are generated in close association with the developing vascular system. In the blood islands of the yolk sac, where the earliest EPCs appear, both HSC and EPC lineages arise almost simultaneously from extraembryonic mesoderm, forming structures in which primitive erythrocytes are surrounded by a layer of angioblasts that give rise to differentiated ECs (Kubo, H. and Alitalo, K., 2003). Transplantation of EPCs can successfully enhance vascular development by in situ differentiation and proliferation within ischemic organs (Kalka, C. et al, 2000).

EPCs display properties similar to those of embryonic angioblasts, which can be defined as migratory ECs with the capacity to circulate, prolifereature, and differentiate into mature ECs, but which have not yet acquired the characteristic mature endothelial markers and have not yet formed a lumen (Peichev, M. et al 2000). EPCs express markers such as, but not limited to, vascular endothelial growth factor receptor-2 (VEGFR-2; KDR; Flk-1), Tie-1, Tie-2, CD31 (PE-CAM-1), E-selectin, and vascular endothelial-cadherin (Rafli, S. 2000). These markers are also found on mature endothelium. EPCs also exhibit characteristics similar to HSCs, such as, for example, CD34 and AC133. Rehman and coworkers describe one such population from peripheral blood that is derived from monocyte/macrophages, and secretes angiogenic growth factors such as but not limited to VEGF, HGF, G-CSF, and GM-CSF (Rehman, J. et al, 2003). This population of EPCs has been shown to express the CD14, Mac-1, and CD11c markers, and to a lesser extent, VD-cadherin, AC133, and c-kit.

VI. Smooth Muscle Progenitor Cells

Smooth muscle progenitor cells (SPCs) can also be used in methods and compositions of the invention. SMCs within the neointima of the vessel wall are believed to originate from circulating smooth muscle progenitor cells (SPCs) of the bone marrow. Simper and coworkers have isolated human mononuclear cells and cultured them on collagen type I matrix in the presence of endothelial growth medium and PDGF-BB (Simper, D. et al 2002). These cells expressed smooth muscle cell-specific actin, myosin heavy chain, calponin, CD34, Flt1, and Flk1, among others, but were negative for Tie-2 receptor.

Other cell types, termed "mesangioblasts", are vessel-derived stem cells that can be induced to differentiate into mesodermal cell types, including smooth muscle. Studies comparing their gene expression profiles in the absence of differentiating factors, such as TGF-β, indicate that two transcription factors, msx2 and necdin, are highly overexpressed in SMCs compared to undifferentiated stem cells, and can induce a plurality of smooth muscle markers (Brunelli, S. et al 2004).

In embryonic tissues, the most well studied SMC precursor is the cardiac neural crest stem cell (Hirschi, K. K. et al, 2004). Smooth muscle differentiation in the neural crest lineage can be controlled by factors such as, but not limited to, Pax3, Tbx1, FoxC1, and serum response factor. These factors interact with numerous other factors in the local microenvironment, such as the BMPs, Wnts, endothelin-1, and FGF-8. Additional sources of multipotent cells that can be used to generate SMCs from progenitors include proepicardial cells and possibly EPCs.

Culture Conditions of the Present Invention

In one embodiment, stem cells or the progenitors thereof are induced to differentiate into endothelial and smooth muscle lineages prior to admixing with the matrix. Initially, the stem cells are maintained and allowed to expand in culture medium that is well established in the art and commercially available from the American Type Culture Collection (ATCC). Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®. It is within the skill of one in the art to modify or modulate concentrations of media and media supplements as necessary for the cells used. It will also be apparent that many media are available as a low-glucose formulation, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade.

Additional supplements can also be used advantageously to supply the cells with the necessary trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin. Antibiotic and antimycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be advantageously used in cell culture and include, but are not limited to D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. One embodiment uses dexamethasone.

Lipids and lipid carriers can also be used to supplement cell culture media, depending on the type of cell and the fate of the differentiated cell. Such lipids and carriers can include, but are not limited to cyclodextrin ($\alpha$, $\beta$, $\gamma$), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. One embodiment uses linoleic acid conjugated to albumin.

Also contemplated is the use of feeder cell layers. Feeder cells are used to support the growth of fastidious cultured cells, including stem cells. Feeder cells are normal cells that have been inactivated by γ-irradiation. In culture, the feeder layer serves as a basal layer for other cells and supplies important cellular factors without further growth or division of their own (Lim, J. W. and Bodnar, A., 2002). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability, and expansion of stem cells. In many cases, feeder cell layers are not necessary to keep the stem cells in an undifferentiated, proliferative state, as leukemia inhibitory factor (LIF) has anti-differentiation properties. Often, supplementation of a defined concentration of LIF is all that is necessary to maintain stem cells in an undifferentiated state.

Cells in culture can be maintained either in suspension or attached to a solid support, such as extracellular matrix components. Stem cells often require additional factors that encourage their attachment to a solid support, such as type I, type II, and type IV collagen, concanavalin A, chondroitin sulfate, fibronectin, "superfibronectin" and fibronectin-like polymers, gelatin, laminin, poly-D and poly-L-lysine, thrombospondin, and vitronectin. Preferred embodiments utilize fibronectin.

The maintenance conditions of stem cells can also contain cellular factors that allow stem cells, such as MAPCs, to remain in an undifferentiated form. Specifically, these cellular factors or components allow the stem cells to constitutively express Oct 3/4 (Oct 3A), maintain high levels of telomerase, and remain negative for CD44, MHC class I and MHC class II expression. It is advantageous under conditions where the cell must remain in an undifferentiated state of self-renewal for the medium to contain epidermal growth factor (EGF), platelet derived growth factor (PDGF), leukemia inhibitory factor (LIF), and combinations thereof. It is apparent to those skilled in the art that supplements that allow the cell to self-renew but not differentiate must be removed from the culture medium prior to differentiation.

Differentiation to ECs can occur when VEGF or other angiogenic factors are added to the culture medium. Other differentiation factors can be similarly employed to induce stem cells to become SMCs, such as PDGF-BB. Angiogenic factors include, but are not limited to, adrenomedullin, acidic fibroblast growth factor (aFGF), angiogenin, angiotensin-1 and -2, betacellulin, basic fibroblast growth factor (bFGF), corpus luteum angiogenic factor (CLAF), endothelial-cell derived growth factor (ECDGF), Factor X and Xa, HB-EGF, PD-ECGF, PDGF, angiomodulin, angiotropin, angiopoetin-1, prostaglandin E1 and E2, steroids, heparin, 1-butyryl-glycerol, nicotinic amide, and tumor necrosis factor $\alpha$. Embodiments of the invention utilize VEGF as a differentiation factor for ECs, and PDGF-BB for SMCs.

Stem cell lines and other fastidious cells like ECs and SMCs often benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Monitoring the progress of EC and SMC differentiation can involve, for example, screening for expression of genetic markers of EC and SMC differentiation. Genetic markers of ECs are well known in the art, and include vWF, acLDL uptake, β-catenin, γ-catenin, connexin-40, connexin 43, ZO-1, c-Kit, CD31 (PECAM-1), CD62P, CD62L, CD62E, $\alpha$V$\beta$3, $\alpha$v$\beta$5, E-cadherin, VE-cadherin, Flt1, Flk1 (VEGF-R2), Tie/Tek, VCAM-1, and CD 105 (Jaffe, E. A. et al, 1974; Stein, O. and Stein, Y., 1976; Tao, Y. S. et al, 1996; Lim, M. J. et al, 2001; Van Rijen, H. et al, 1997; Watson, P. M. et al, 1991; Buzby, J. S. et al, 1994; Albelda, S. M. et al, 1990; Johnston, G. I. et al, 1989; Friedlander, M. et al, 1995; Bevilacqua, M. P. et al, 1989; Buhrer, C. et al, 1990; Lawler, J. and Hynes, R. O., 1989; Bavisotto, L. M. et al, 1990; Breviario, F. et al, 1995; Waltenburger, J. et al, 1994; Chiang, M. K. and Flanagan, J. G., 1995; Partanen, J. et al, 1992; Dunont, D. J. et al, 1993; Osborn, L. et al, 1989; Gougos, A. and Letarte, M., 1990; reviewed in Bachetti, T. and Morbidelli, L., 2000). Genetic markers of SMCs are also known, and can include, but are not limited to, desmin, smooth muscle $\alpha$-actin, calponin, smoothelin, and smooth muscle myosin heavy chain and light chains (Gabbiani, G. et al, 1981; Birukov, K. G. et al, 1991; Ratajska, A. et al, 2001; reviewed in Sobue, K. et al, 1999). It will be apparent to those skilled in the art that not all markers listed above are restricted to ECs or SMCs.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e. formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. One embodiment of the invention envisions the use of FACS to identify and separate cells based on cell-surface antigen expression.

The present invention is additionally described by way of the following illustrative, non-limiting Examples that provide a better understanding of the present invention and of its many advantages.

EXAMPLES

Example 1

Culture and Differentiation Conditions for MAPCs

MAPC Isolation and Culture Conditions

Bone marrow (BM) was obtained from 55 healthy volunteers donors (age 2-50 years) after informed consent using guidelines from the University of Minnesota Committee on the use of Human Subject in Research. MAPCs were generated as previously described (Furcht et al.). Briefly, BM mononuclear cells (BMMNC) were depleted of $CD45^+$ and glycophorin-$A^+$ cells using micromagnetic beads (Miltenyii Biotec, Sunnyvale, Calif.). $CD45^-$/$GlyA^-$ cells ($5\times10^3$ cells) diluted in 200 μL expansion medium comprising 58% low-glucose Dulbecco's minimal essential medium, low-glucose formulation (DMEM-LG) (Gibco-BRL, Grand Island, N.Y.), 40% MCDB-201 (Sigma Chemical Co, St Louis, Mo.), supplemented with 1× insulin-transferrin-selenium (ITS), 1× linoleic-acid bovine serum albumin (LA-BSA), $10^{-8}$M Dexamethasone, $10^{-4}$M ascorbic acid 2-phosphate (all from Sigma), 100 U penicillin and 1,000 U streptomycin (Gibco) and 10% FCS (Hyclone Laboratories, Logan, Utah) with 10 ng/ml of epidermal growth factor (EGF; Sigma) and 10 ng/ml PDGF-BB (R&D Systems, Minneapolis, Minn.) were plated in wells of 96 well plates that had been coated with 5 ng/ml of fibronectin (FN; Sigma). Medium was exchanged every 4-6 days. Once wells were >40-50% confluent, adherent cells were detached with 0.25% trypsin-EDTA (Sigma) and replated at 1:4 dilution in bigger culture vessels, again coated with 5 ng/ml fibronectin and MAPC expansion medium to maintain cell densities between 2 and $8\times10^3$ cells/$cm^2$.

Differentiation Conditions and Characterization

To induce differentiation to ECs, MAPC were replated at $1-2\times10^4$ cells/$cm^2$ in FN coated culture vessels or chamber slides in 60% low-glucose Dulbecco's minimal essential medium (DMEM-LG) (Gibco-BRL, Grand Island, N.Y.), 40% MCDB-201 (Sigma Chemical Co, St Louis, Mo.), supplemented with IX insulin-transferrin-selenium (ITS), 1× linoleic-acid bovine serum albumin (LA-BSA), $10^{-8}$M Dexamethasone, $10^{-4}$M ascorbic acid 2-phosphate (all from Sigma), 100 U penicillin and 1,000 U streptomycin (Gibco) with 10 ng/mL vascular endothelial growth factor (VEGF; a kind gift from Dr. S. Ramakrishna, U. of Minnesota). In some instances, fetal calf serum (FCS; Hyclone Laboratories, Logan, Utah) was added. Cultures were maintained by media exchange every 4-5 days. Cells were subcultured after day 9 at a 1:4 dilution under the same culture conditions for 20+ population doublings. Most populations used for the vessels have been cultured for more than 5 population doublings.

Medium for Differentiation of Human MAPC Endothelium

For every 100 ml:

| Description | Stock Concentration | Final Concentration | Amount |
|---|---|---|---|
| VEGF | 10 μg/ml | 10 ng/ml | |
| Serum-free | N/A | | 100 ml |

For every 100 ml: (serum free medium)

| Description | Stock Concentration | Final Concentration | Amount |
|---|---|---|---|
| Dexamethasone | 0.25 mM (in $H_2O$) | 0.05 μM | 20 μl |
| ITS | 100 × | 1 × | 1 ml |
| Linoleic acid-BSA | 100 mg/ml | 1 mg/ml | 1 ml |
| DMEM-LG | N/A | N/A | 62 ml |
| MCDB-201 | Dissolve in $H_2O$, adjust pH to 7.1-7.2 | Dissolve in $H_2O$, adjust pH to 7.1-7.2 | 40 ml |
| Penicillin/Streptomycin | 100 × | 1 × | 1 ml |
| L-Ascorbic Acid | 100 × (10 mM in PBS) | 1 × (0.1 mM in PBS) | 1 ml |

Endothelial differentiation with VEGF was induced by culturing 60-80% (12,500-20,000 cells/$cm^2$) confluent cultures of MAPCs in serum free medium (58% DMEM-LG, 40% MCDB-201, supplemented with 1×ITS, 1×LA-BSA, $10^{-8}$M Dexamethasone, $10^{-4}$M ascorbic acid 2-phosphate, 100 U penicillin, 1,000 U streptomycin) and 10 ng/mL VEGF.

Table 1 summarizes the cell-surface markers expressed on ECs derived from MAPCs and the antibodies used to detect them.

TABLE 1

| Antibodies against cell surface markers expressed on MAPC-derived ECs | | | | | |
|---|---|---|---|---|---|
| Cell Surface Marker | Function | Fluorescent conjugate | Company | Ig Isotype | Flow cytometry |
| VWF | | N/A | Santa Cruz | | |
| β-catenin | Connects to cadherins on cytoskeleton | N/A | Chemicon | | |
| γ-catenin | Connects to cadherins on cytoskeleton | N/A | Chemicon | | |

TABLE 1-continued

Antibodies against cell surface markers expressed on MAPC-derived ECs

| Cell Surface Marker | Function | Fluorescent conjugate | Company | Ig Isotype | Flow cytometry |
|---|---|---|---|---|---|
| Connexin-40 | Gap junction protein | N/A | Chemicon | | |
| Connexin-43 | Gap junction protein | N/A | Sigma | | |
| ZO-1 | Tight junction protein | N/A | Chemicon | IgG | |
| CD117 (c-Kit) | Transmembrane tyrosine-kinase receptor | R-phycoerythrin | Pharmingen | IgG2b | 10 μl/1 33 10$^6$ |
| CD62P (p-selectin) | Glycoprotein cell adhesion molecule | FITC | Chemicon | IgG1 | |
| CD62E (e-selection) | Glycoprotein cell adhesion molecule | FITC | Chemicon | IgG2a | 1:20 |
| CD62L (l-selectin) | Glycoprotein cell adhesion molecule | FITC | Sigma | IgG2b | |
| αVβ3 | Vitronectin (integrin) receptor | FITC | Chemicon | IgG1 | |
| αVβ5 | Integrin | Phycoerythrin | Chemicon | IgG1 | |
| E-cadherin | Epi. Cell characterization | N/A | Chemicon | IgG1 | |
| VE-cadherin | Cell adhesion molecule | N/A | Chemicon | IgG2a | |
| Flk1 (VEGF-R2) | Transmembrane tyrosine-kinase receptor | Phycoerythrin | Chemicon | IgG2a | |
| VCAM-1 | Recognizes surface ligand VLA-4 | FITC | Chemicon | IgG1 | |
| PECAM-1 LDL uptake (+) | Human surface PECAM | FITC | Chemicon | IgG1 | |

Figure 2:
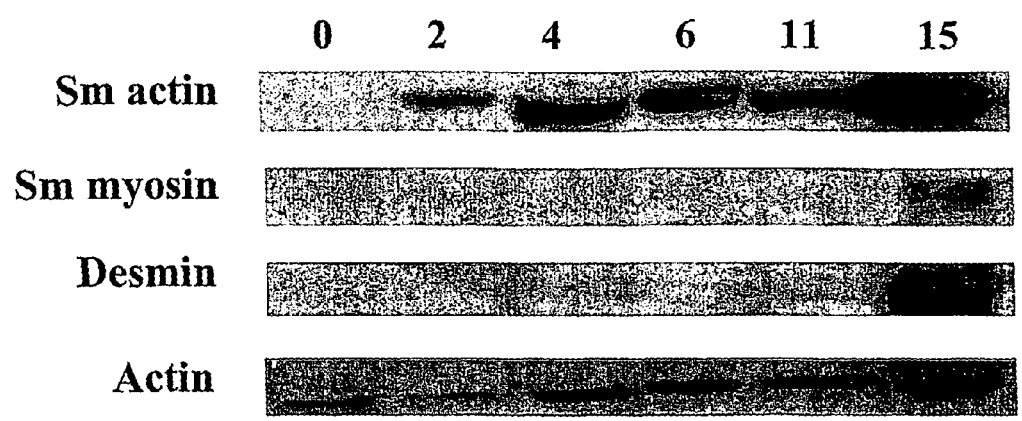
FIG. 2 shows an immunoblot of SMC markers, α-actin, myosin, desmin, and β-actin, expressed by mesenchymal stem cells induced with platelet-derived growth factor-BB (PDGF-BB) to differentiate into smooth muscle.
Figure 3:
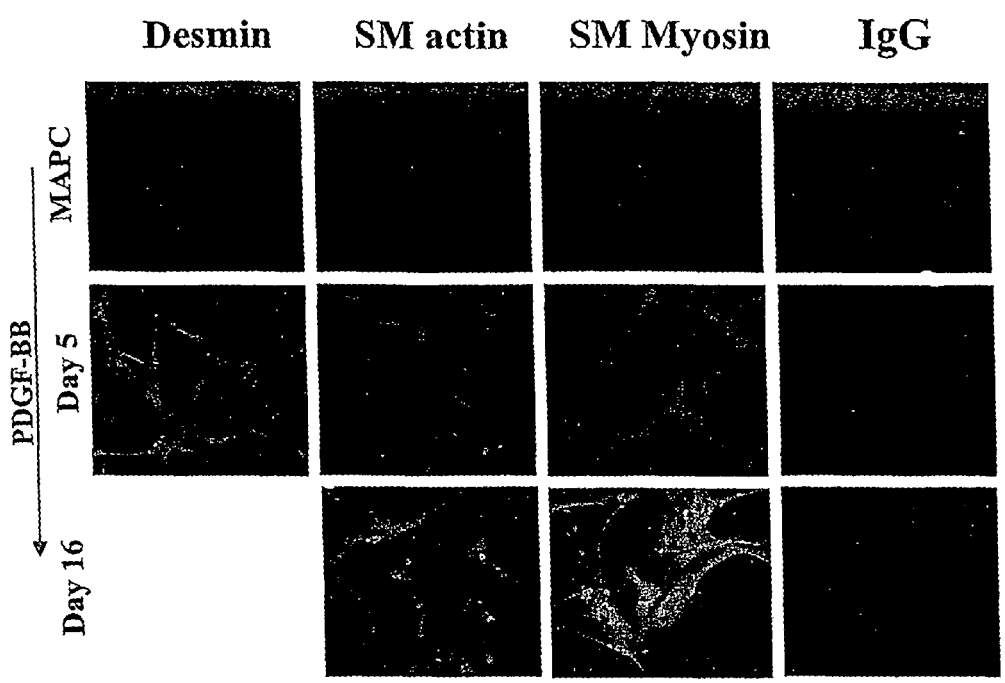
FIG. 3 shows smooth muscle development from multipotent adult progenitor cells (MAPCs). Cultured in the presence of PDGF-BB, MAPCs can be induced to differentiate into SMCs that express SMC cell surface markers desmin, smooth muscle actin, and smooth muscle myosin. IgG was used as a negative control.

SMCs can also be induced by culturing MAPCs in serum-free medium, without growth factors, supplemented with high concentrations (about 50 to about 200 ng/ml, preferably about ng/ml) of platelet-derived growth factor (PDGF). Cells should preferably be confluent at initiation of differentiation. Terminally differentiated SMCs can be identified by detecting expression of desmin, smooth muscle specific actin, and smooth muscle specific myosin by standard methods known to those of skill in the art. Smooth muscle actin was detected from day two onwards and smooth muscle myosin after 14 days. Approximately 70% of cells stained positive with anti-smooth muscle actin and myosin antibodies. A presence of desmin was seen after 6 days. FIG. 2 is an immunoblot demonstrating that SMC markers α-actin, myosin, desmin, and β-actin (control) are expressed by MAPCs induced with platelet-derived growth factor-BB. Similarly, FIG. 3 shows the development of SMCs from MAPCs cultured in the presence of PDGF-BB. Desmin, smooth muscle actin, and smooth muscle myosin were used as SMC cell surface markers. Immunoglobulin G was used as a negative control.

Example 2

Formation of a Blood Vessel by Incorporation of Cells in a Matrix

In this Example, a blood vessel is engineered by incorporation of SMCs and ECs in a fibrin gel tube with VEGF stimulus in the lumen.

Three solutions are required to make a fibrin gel: fibrinogen solution, cell suspension, and thrombin solution. The fibrinogen solution is composed of 5 mg/mL of fibrinogen in 20 mM HEPES buffered saline while the thrombin solution is 150 units of thrombin in 1% water by volume and 9% saline by volume in serum free culture medium with a 0.004 M $CaCl_2$ catalyst. The cell suspension is at six times the final concentration; therefore, the suspension is at $1.5 \times 10^6$ cell/mL to have a final concentration of $0.25 \times 10^6$ cells/mL. The fibrinogen solution, the cell suspension, and the thrombin solution are mixed at a ratio of 4:1:1 by volume and gel in less than one hour at 37° C.

The mold to form a tubular fibrin gel for co-culturing cells is composed of a tubular porous polyethylene mandrel (70 μm pore size), rubber stoppers, and a tubular outer casing as shown in FIG. 5. Rubber stoppers are placed on the ends of the porous mandrel. The mandrel with stoppers is dipped into a 2% agarose solution to provide a nonstick surface on the outer surface of the polyethylene mandrel. The coated mandrel with stoppers is then placed into an outer casing made of plastic or glass. A needle is inserted between the rubber stopper and the outer casing at one end to allow air to escape as the space is filled with solution. Once the fibrinogen solution, cell suspension, and thrombin solution are mixed, they are injected between the outer casing and the porous mandrel using a needle and syringe. The needles are removed and the solution is then allowed to gel at 37° C. in an incubator. A plunger is used to gently push the rubber stoppers, porous mandrel, and fibrin gel out of the outer casing and into a container containing culture medium. See FIG. 4 for a schematic representation of the incorporation and organization process.

Rat neonatal smooth muscles (r-neo-SMCs), at a final concentration of $0.25 \times 10^6$ cells/mL, human multipotent adult progenitor cell-derived ECs (h-MAPC-ECs), at a final concentration of $0.05 \times 10^6$ cells/mL, and human multipotent adult progenitor cell-derived SMCs (h-MAPC-SMCs), at a final concentration of $0.05 \times 10^6$ cells/mL, were used to make sixteen constructs. Two constructs contained r-neo-SMCs and were given TGF-β culture medium, while two constructs contained r-neo-SMCs and h-MAPC-ECs and were given TGF-β culture medium. Two constructs containing h-MAPC-SMCs were given TGF-β medium. Four constructs containing r-neo-SMCs were given both TGF-β and VEGF culture medium, while four constructs containing r-neo-SMC and h-MAPC-ECs were given both TGF-β and VEGF culture medium. Two constructs containing h-MAPC-EC were given both TGF-β and culture medium. The constructs are summarized below:

| No. of Constructs | Cell Type(s) | Culture Medium |
|---|---|---|
| 2 | r-neo-SMC | TGF-β |
| 2 | r-neo-SMC and h-MAPC-EC | TGF-β |
| 2 | h-MAPC-SMC | TGF-β |
| 4 | r-neo-SMC | TGF-β and VEGF |
| 4 | r-neo-SMC and h-MAPC-EC | TGF-β and VEGF |
| 2 | h-MAPC-EC | TGF-β and VEGF |

The TGF-β culture medium consisted of high glucose DMEM, 10% fetal bovine serum, 2 mg/mL amino caproic acid, 2 µg/mL insulin, and 2.5 ng/mL transforming growth factor β (TGF-β). The VEGF culture medium consisted of high glucose DMEM, 10% fetal bovine serum, 2 mg/mL amino caproic acid, 2 µg/mL insulin, and either 50 ng/mL of vascular endothelial growth factor (VEGF) for the first week of culture or 5 ng/mL of VEGF for subsequent weeks. For the final night of culture for all samples, a medium containing high glucose DMEM, 10% fetal bovine serum, 2 mg/mL amino caproic acid, 2 µg/mL insulin, and 10 µg/mL Dil-Ac-LDL was used to assist in immunostaining.

The top stoppers were removed after the samples were ejected from the mold, and the culture medium was changed three times a week with 5-mL (approximately three-fourths of the total volume of medium) of the TGF-β culture medium being removed and replaced each time. For samples containing ECs, 0.5 mL of the VEGF culture medium (at concentrations 50 ng/mL for the first week and 5 ng/mL for subsequent weeks) was injected into the lumen of the porous mandrel with a syringe at each changing of the culture medium. All samples were cultured in a 5% $CO_2$ incubator. Sterile forceps were used to loosen the gel from the ends of the mandrel as necessary during the first week to allow compaction of the gel to occur.

The dimensions of the molds used to make the samples were a 0.25 inch outer diameter, 0.156 inch inner diameter, 2 inch long 70 µm porous hollow polyethylene mandrel; two rubber plunger tips from 3 cc syringes inside two rubber plunger tips from 6 cc syringes; and a plastic cylinder longer than 2 inches from a 6 cc syringe.

After one week, one construct with r-neo-SMCs receiving TGF-β and VEGF culture mediums as well as one construct with r-neo-SMCs and h-MAPC-ECs receiving TGF-β and VEGF culture media were harvested and frozen in OCT for frozen tissue sectioning. After two weeks, one construct with r-neo-SMCs receiving TGF-β and VEGF culture media and h-MAPC-ECs receiving TGF-β and VEGF culture media were harvested and frozen in OCT for frozen tissue sectioning. After four weeks, all remaining samples were harvested and frozen in OCT for frozen tissue sectioning.

Figure 6:
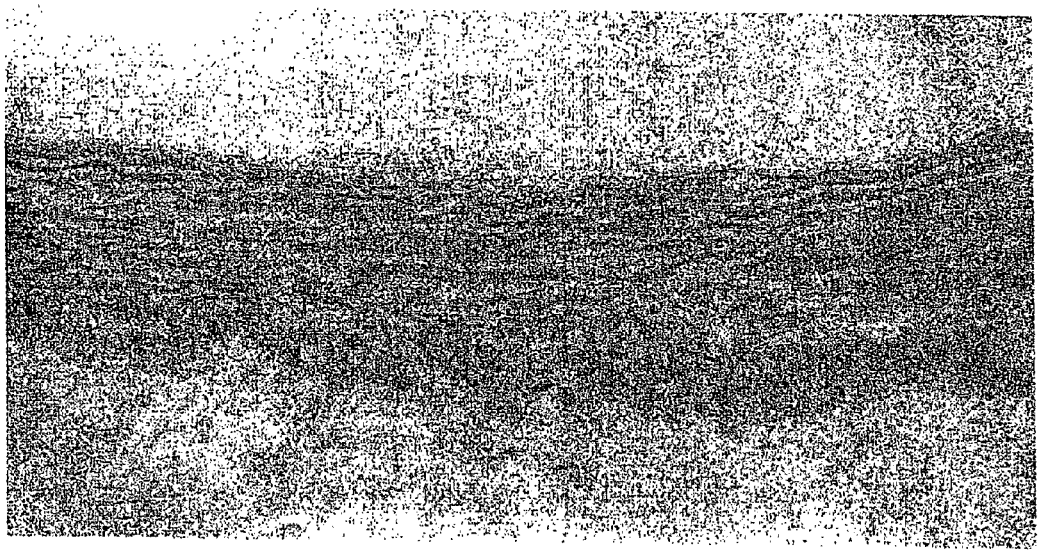
FIG. 6 shows Masson's Trichrome Staining of a rat aorta. Green corresponds to collagen; light red stains cell cytoplasm and muscle fibers; purple corresponds to cell nuclei; and dark red marks fibrin staining.
Figure 7:
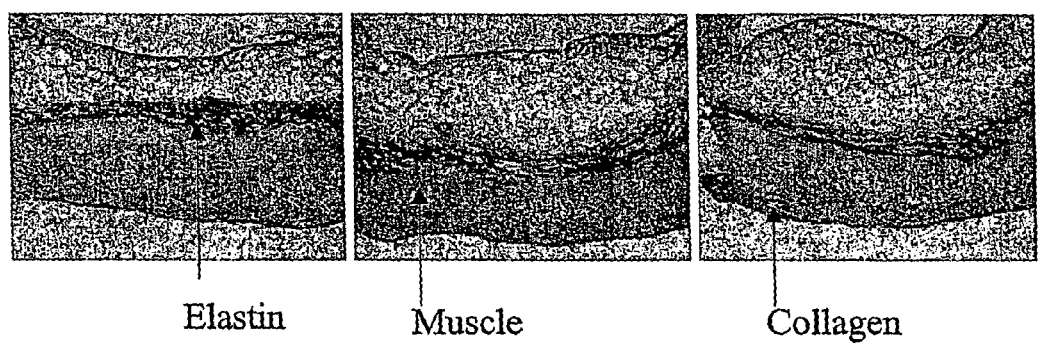
FIG. 7 shows Verhoeff's Von Gieson Staining of a tissue-engineered medial layer formed by the process in FIG. 4.

Tissues were sectioned into 10 µm slices. Masson's Trichrome staining (FIG. 6) and Verhoeff's Van Gieson staining (FIG. 7) was used to assess extracellular matrix production, and immunohistological staining was performed to detect vWF, LDL, collagen type IV, smooth muscle actin, and DAPI (4,6-diaminophenylindole) to ascertain the relative location of the ECs and the SMCs.

Example 3

Characterization of Layered Circumferential Vascular Structure

After culturing the constructs from Example 2 on the agarose-coated porous polyethylene tube for 7 days, ECs were mainly located close to the lumenal surface (FIG. 8), however the cells were still somewhat disorganized, as seen in FIG. 9. After 3 weeks of culture, the cells began to align and form prototypical layers, as detected by vWF staining, LDL uptake, and DAPI staining (FIG. 10). ECs were seen close to the lumenal surface. FIG. 11A show a cross-section of the entire construct at lower magnification immunostained for α-smooth muscle-actin (red), collagen type IV (green), and DAPI (blue). SMCs populated the interior of the construct and ECs were absent from the outer surface, which was surrounded by medium that was not supplemented with VEGF, indicating that ECs can be selectively localized to surfaces after incorporation by presenting a concentration gradient of VEGF, presumably by a chemomitoattractant response. FIGS. 11B and C show marked organization of the cellular layers, especially of a section near the lumenal surface of the construct after 5 weeks of incubation. The vessel was immunostained for low-density lipoprotein (red), collagen type IV (green), and DAPI (purple—stains cell nuclei).

In summary, ECs localized to the lumenal surface of the tubular constructs, which was the surface in contact with the VEGF-supplemented medium. As the SMCs commenced to remodel the fibrin into cell-derived ECM, the nascent endothelium matured. Additionally, type IV collagen staining shows the presence of basement membrane formation between the two cell layers. Formation of the basement membrane should confer endothelial stability and paracrine factor effects that lead to a quiescent endothelium as well as improved ECM formation by the tissue cells (and hence better construct properties).

Table 2 is a summary of the expression pattern of cell surface markers found on ECs derived from MAPCs.

TABLE 2

Expression profile for cell surface molecules of endothelium

| Cell Surface Markers | Days Expressed | Working Dilutions |
|---|---|---|
| Flk1 | Low to d9-d18 | 1:50 |
| Flt1 | Low to d9-d18 | 1:50 |
| VE-cadherin | d3-d18 | 1:50 |
| AC133 | Low before d3 | 1:50 |
| αVβ5 | d3-d14 | 1:50 |
| αVβ3 | d3-d14 | 1:50 |
| Tie | After d7 | 1:50 |
| Tek | After d3 | 1:50 |
| vWF | After d9 | 1:50 |
| CD31 | >d14 | 1:50 |
| CD36 | >d14 | 1:50 |
| CD62-P | >d14 | 1:50 |
| ZO-1 | >d14 | 1:50 |
| β-catenin | >d14 | 1:50 |
| γ-catenin | >d14 | 1:50 |

ECs were replated at a cell density of 7000-9000 cells/cm$^2$.

Although the foregoing invention has been described in some detail by way of illustrations and examples for purposes of clarity and understanding, it will be apparent to those skilled in the art that certain changes and modifications can be practiced. Therefore, the description and examples should not be construed as limiting the scope of the invention.

REFERENCES

Albeda, S. M., Oliver, P. D., Romer, L. H., and Buck, C. A.: "EndoCAM: a novel endothelial cell-cell adhesion molecule" (1990) *J. Cell Biol.* 110: 1227-37.

Asahara, T., Murohara, T., Sullivan, A., Silver, M., van der Zee, R., Li, T., Witzenbichler, B., Schatteman, G. & Isner, J.: "Isolation of putative progenitor endothelial cells for angiogenesis" (1997) *Science* 275, 964-967.

Bachetti, T. and Morbidelli, L.: "Endothelial cells in culture: a model for studying vascular functions" (2000) *Pharm. Res.* 42: 9-19.

Badylak, S., Liang, A., Record, R., Tullus, R., and Hodde, J.: "Endothelial cell adherence to small intestinal submucosa: an acellular bioscaffold" (1999) *Biomaterials* 20: 2257-2263.

Barocas, V. H., Girton, T. S., and Tranquillo, R. T.: "Engineered alignment in mediaequivalents: Magnetic prealignment and mandrel compaction". (1998) *J. Biomech. Eng.* 120(5): 660-666.

Bavisotto, L. M., Schwartz, S. M., and Heimark, R. L.: "Modulation of Ca2(+)-dependent intercellular adhesion in bovine aortic and human umbilical vein endothelial cells by heparin-binding growth factors." (1990) *J. Cell Physiol.* 143: 39-51.

Bevilacqua, M. P., Stengelin, S., Gimbrone, M. A. Jr, and Seed, B.: "Endothelial leukocyte adhesion molecule 1: an inducible receptor for neutrophils related to complement regulatory proteins and lectins" (1989) *Science* 243: 1160-5.

Birukov, K. G., Stepanova, O. V., Nanaev, A. K., and Shirinsky, V. P.: "Expression of calponin in rabbit and human aortic smooth muscle cells" (1991) *Cell Tissue Res.* 266: 579-84.

Breviario, F., Caveda, L., Corada, M., Martin-Padura, I., Navarro, P., Golay, J., Introna, M., Gulino, D., Lampugnani, M. G., and Dejana, E.: "Functional properties of human vascular endothelial cadherin (7B4/cadherin-5), an endothelium-specific cadherin" (1995) *Arterioscler. Thromb. Vasc. Biol.* 15: 1229-39.

Bruder, S., et al., U.S. Pat. No. 5,736,396

Buhrer, C., Berlin, C., Thiele, H. G., Hamann, A.: "Lymphocyte activation and expression of the human leucocyte-endothelial cell adhesion molecule 1 (Leu-8/TQ1 antigen)" (1990) *Immunology* 71: 442-8.

Buzby, J. S., Knoppel, E. M., and Cairo, M. S.: "Coordinate regulation of Steel factor, its receptor (Kit), and cytoadhesion molecule (ICAM-1 and ELAM-1) MRNA expression in human vascular endothelial cells of differing origins" (1994) *Exp. Hematol.* 22: 122-9.

Caplan, A., et al., U.S. Pat. No. 5,486,359

Caplan, A., et al., U.S. Pat. No. 5,811,094

Caplan, A., et al., U.S. Pat. No. 5,837,539

Cassiede P., Dennis, J. E., Ma, F., Caplan, A. I.: "Osteochondrogenic potential of marrow mesenchymal progenitor cells exposed to TGF-beta 1 or PDGF-BB as assayed in vivo and in vitro". (1996) *J Bone Miner Res.* 9:1264-73.

Celio, H., Lozano, J., Cabibil, H., Ballast, L., and White, J. M.: "Self-Assembly of Fluid-Filled $KHCO_3$ Microfibers" (2003) *J. Am. Chem. Soc.* 125: 3302-3310.

Chiang, M. K., and Flanagan, J. G.: "Interactions between the Flk-1 receptor, vascular endothelial growth factor, and a cell-surface proteoglycan identified with a soluble receptor reagent" (1995) *Growth Factors* 12: 1-10.

Choi, K.: "The Hemangioblast: A Common Progenitor of Hematopoietic and Endothelial Cells" (2002) *J. Hematother. Stem Cell Res.* 11: 91-101.

Conte, M. S.: "The ideal small arterial substitute: a search for the Holy Grail?" (1998) *FASEB J.* 12(1): p. 43-5.

Diglio, C. A., P. Grammas, F. Giacomelli, and J. Wiener, 1989, "Angiogenesis in rat aorta ring explant cultures," Lab Invest. Vol. 60, pp. 523-31.

DiGuisto, et al., U.S. Pat. No. 5,681,599

Donovan, P. J. and Gearhart, J.: "The end of the beginning for pluripotent stem cells" (2001) *Nature* 414: 92-97.

Dumont, D. J., Gradwohl, G. J., Fong, G. H., Auerbach, R., and Breitman, M. L.: "The endothelial-specific receptor tyrosine kinase, tek, is a member of a new subfamily of receptors" (1993) *Oncogene* 8: 1293-301.

Ema, M., Faloon, P., Zhang, W. J., Hirashima, M., Reid, T., Stanford, W. L., Orkin, S., Choi, K., and Rossant, J.: "Combinatorial effects of Flk1 and Tal1 on vascular and hematopoietic development in the mouse" (2003) *Genes Dev.* 17: 380-93.

Fei, R., et al., U.S. Pat. No. 5,635,387

Fridenshtein, A.: "Stromal bone marrow cells and the hematopoietic microenvironment". (1982) *Arkh Pathol* 44:3-11.

Friedlander, M., Brooks, P. C., Shaffer, R. w., Kincaid, C. M., Varner, J. A., and Cheresh, D. A.: "Definition of two angiogenic pathways by distinct alpha v integrins" (1995) *Science* 270: 1500-2.

Furcht et al. International Application No. PCT/US00/21387

Gabbiani, G., Schmid, E., Winter, S., Chaponnier, C., de Ckhastonay, C., Vandekerckhove, J., Weber, K., and Franke, W. W.: "Vascular smooth muscle cells differ from other smooth muscle cells: predominance of vimentin filaments and a specific alpha-type actin" (1981) *Proc. Natl. Acad. Sci. USA* 78: 298-302.

Gammill, L. S. and Bonner-Fraser, M.: "Genomic analysis of neural crest induction" (2002) *Development* 129: 5731-5741.

Girton, T. S., Oegema, T. R. Grassl, E. D. Isenberg, B. C. and Tranquillo, R. T.: "Mechanisms of stiffening and strengthening in media-equivalents fabricated using glycation". (2000) *J. Biomech. Eng.* 122: 216-2

Gronthos, S., Graves, S., Ohta, S., and Simmons, P.: "The STRO-1+ fraction of adult human bone marrow contains the osteogenic precursors". (1994) *Blood* 84: 4164-73.

Gougos, A., and Letarte, M.: "Primary structure of endoglin, an RGD-containing glycoprotein of human endothelial cells" (1990) *J. Biol. Chem.* 265: 8361-4.

Hardman, J. G., Limbird, L. E., Molinoff, P. B., Ruddon, R. W., and Gilman, A, eds. *Goodman and Gilman's The Pharmacological Basis of Therapeutics* $9^{th}$ Edition, (1996) McGraw Hill, New York.

Hellstrom, M., Kalen, M., Lindahl, P., Abramsson, A., and Betsholtz, C.: "Role of PDGF-B and PDGFR-beta in recruitment of vascular smooth muscle cells and pericytes during embryonic blood vessel formation in the mouse" (1999) *Development* 126(14): 3047-55.

Hill, B., Rozler, E., Travis, M., Chen, S., Zannetino, A., Simmons, P., Galy, A., Chen, B., Hoffman, R.: "High-level expression of a novel epitope of CD59 identifies a subset of CD34+ bone marrow cells highly enriched for pluripotent stem cells". (1996) *Exp Hematol.* 8:936-43.

Hirschi, K. K., Rohovsky, S. A., D'Amore, P. A.: "PDGF, TGF-β and heterotypic cell-cell interactions mediate the recruitment and differentiation of 10T1/2 cells to a smooth muscle cell fate" (1998) *J. Cell Biol.* 141: 805-814.

Hirschi, K. K., Rohovsky, S. A., Beck, L. H., Smith, S. R., and D'Amore, P. A.: "Endothelial cells modulate the proliferation of mural cell precursors via PDGF-BB and heterotypic cell contact" (1999) *Circ. Res.* 84: 298-305.

Huynh, T., Abraham, G. Murray, J. Brockbank, K. Hagen, P. O. and Sullivan, S.: "Remodeling of an acellular collagen graft into a physiologically responsive neovessel" (1999) *Nat. Biotechnol.* 17(11): 1083-6.

Ishisaki, A., Hayashi, H., Li, A. J., and Imamura, T.: "Human umbilical vein endothelium-derived cells retain potential to differentiate into smooth muscle-like cells" (2003) *J. Biol. Chem.* 278: 1303-9.

Jackson, K., Majka, S. M., Wang, H., Pocius, J., Hartley, C., Majesky, M. W., Entnan, M. L., Michael, L., Hirschi, K. K. & M. A., G. "Regeneration of ischemic cardiac muscle and vascular endothelium by adult stem cells" (2001) *J Clin Invest* 107: 1395-1402.

Jaffe, E. A., Nachman, R. L., Becker, C. G., Minick, C. R.: "Culture of human endothelial cells derived from umbilical veins. Identification by morphologic and immunologic criteria" (1973) *J. Clin. Invest.* 52(11): 2745-56.

Jaffe, E. A., Hoyer, L. W., and Nachman, R. L.: "Synthesis of von Willebrand factor by cultured human endothelial cells" (1974) *Proc. Natl. Acad. Sci. USA* 71: 1906-9.

Jaiswal, N., Haynesworth, S. E., Caplan, A. I., Bruder, S. P.: "Osteogenic differentiation of purified, culture-expanded human mesenchymal stem cells in vitro" (1997) *J. Cell Biochem.* 64(2): 295-312.

Janin, A., Konttinen, Y. T., Gronblad, M., Karhunen, P., Gosset, D., Malmstrom, M.: "Fibroblast markers in labial salivary gland biopsies in progressive systemic sclerosis" (1990 *Clin. Exp. Rheumatol.* 8(3): 237-42.

Jiang, Y., Vaessen, B., Lenvik, T., Blackstad, M., Reyes, M. & Verfaillie, C. M.: "Multipotent progenitor cells can be isolated from postnatal murine bone marrow, muscle, and brain" (2002) *Exp Hematol.* 30(8): 896-904.

Jiang, Y., Jahagirdar, B., Reyes, M., Reinhardt, R. L., Schwartz, R. E., Chang, H.-C., Lenvik, T., Lund, T., Blackstad, M., Du, J., Aldrich, S., Lisberg, A., Kaushal, S., Largaespada, D. L. & Verfaillie, C. M.: "Pluripotency of mesenchymal stem cells derived from adult marrow" (2002) *Nature* 418: 41-9.

Johnston, G. I., Kurosky, A., and McEver, R. P.: "Structural and biosynthetic studies of the granule membrane protein, GMP-140 from human platelets and endothelial cells" (1989) *J. Biol. Chem.* 264: 1816-23.

Johnstone, B., Hering, T. M., Caplan, A. I., Goldgberg, V. M., Yoo, J. U.: "In vitro chondrogenesis of bone marrow-derived mesenchymal progenitor cells". (1998) *Exp Cell Res.* 1:265-72.

Kalka, C., Masuda, H., Takahashi, T., Kalka-Moll, W. M., Silver, M., Kearney, M., Li, T., Isner, J. M., and Asahara, T.: "Transplantation of ex vivo expanded endothelial progenitor cells for therapeutic neovascularization" (2000) *Proc. Natl. Acad. Sci. USA.* 97(7): 3422-7.

Kawakita, E., et al (2002) *J. Smooth Muscle Res.* 38 (6): J33.

Krause, D. S., Theise, N. D., Collector, M. I., Henegariu, O., Hwang, S., Gardner, R., Neutzel, S. & Sharkis, S. I.: "Multi-organ, multi-lineage engraftment by a single bone marrow-derived stem cell" (2001) Cell 105: 369-77.

Kubo, H. and Alitalo, K.: "The bloody fate of endothelial stem cells" (2003) *Genes Dev.* 17: 322-329.

Lawler, J. and Hynes, R. O.: "An integrin receptor on normal and thrombasthenic platelets that binds thrombospondin" (1989) *Blood* 74: 2022-7.

Lebkowski, J. S., Gold, J., Xu, C., Funk, W., Chiu, C. P., and Carpenter, M. K.: "Human embryonic stem cells: culture, differentiation, and genetic modification for regenerative medicine applications" (2001) *Cancer J.* 7 (Suppl. 2): S83-93.

L'Heureux, N., Germain, L. Labbe, R. and Auger, F. A.: "In vitro construction of a human blood vessel from cultured vascular cells: a morphologic study". (1993) *J. Vasc. Surg.* 17(3): 499-509.

L'Heureux, N., Paquet, S., Labbe, R., Germain, L., and Auger, F. A.: "A completely biological tissue-engineered human blood vessel" (1998) *FASEB J.* 12(1): 47-56.

L'Heureux, N., Stoclet, J. C., Auger, F. A. Lagaud, G. J. Germain, L. and Andriantsitohaina, R.: "A human tissue-engineered vascular media: a new model for pharmacological studies of contractile responses" (2001) *FASEB J.* 15(2): 515-24.

Lim, J. W., and Bodnar, A.: "Proteome analysis of conditioned medium from mouse embryonic fibroblast feeder layers which support the growth of human embryonic stem cells" (2002) *Proteomics* 2(9): 1187-1203.

Lim, M. J., Chiang, E. T., Hechtman, H. B., and Shepro, D.: "Inflammation-induced subcellular redistribution of VE-cadherin, actin, and gamma-catenin in cultured human lung microvessel endothelial cells" (2001) *Microvasc. Res.* 62: 366-82.

Lin, Y., Weisdorf, D. J., Solovey, A. & Hebbel, R. P.: "Origins of circulating endothelial cells and endothelial outgrowth from blood" (2000) *J Clin Invest* 105, 71-7.

Lindahl, P., Hellstrom, M., Kalen, M., Betscholtz, C.: "Endothelial-perivascular cell signaling in vascular development: lessons from knockout mice" (1998) *Curr. Opin. Lipid* 9: 407-411.

Martin, G. R.: "Isolation of a pluripotent cell line from early mouse embryos cultured in medium conditioned by teratocarcinoma stem cells". (1981) *Proc Natl Acad Sci U.S.A.* 12:7634-8.

Masinovsky, B., U.S. Pat. No. 5,837,670

Mayer, J. E., Jr., Shin'oka, T. and Shum-Tim, D.: "Tissue engineering of cardiovascular structures". (1997) *Curr. Opin. Cardiol.* 12(6): p. 528-32

McGlave, et al., U.S. Pat. No. 5,460,964

Minguell, J. J., Erices, A., and Conget, P.: "Mesenchymal Stem Cells" (2001) *Exp. Biol. Med.* 226(6): 507-520.

Morrison, S. J., White, P. M., Zock, C., and Anderson, D. J.: "Prospective identification isolation by flow cytometry and in Vivo self-renewal of multipotent mammalian neural crest stem cells". (1999) *Cell.* 96:737-749.

Nardin, C. and Meier, W.: "Hybrid materials from amphiphilic block copolymers and membrane proteins" (2002) *Rev. Mol. Biotech.* 90: 17-26.

Nerem, R. M.: "Tissue engineering a blood vessel substitute: the role of biomechanics" (2000) *Yonsei Med J.* 41(6): p. 735-9.

Niklason, L. E., Gao, J., Abbott, W. M., Hirschi, K. K., Houser, S., Marini, R., and Langer, R.: "Functional arteries grown in vitro". (1999) *Science* 284(5413): 489-93.

Niklason, L. E.: "Replacement arteries made to order". (1999) *Science* 286(5444): 1493-4.

Niklason, L. E., Abbott, W., Gao, J., Klagges, B., Hirschi, K. K., Ulubayram, K., Conroy, N., Jones, R., Vasanawala, A., Sanzgiri, S., and Langer, R.: "Morphologic and mechanical characteristics of engineered bovine arteries". (2001) *J. Vasc. Surg* 33(3): 628-38.

Oishi, K., Ogawa, Y., Gamoh, S., and Uchida, M. K.: "Contractile responses of smooth muscle cells differentiated from rat neural stem cells" (2002) *J. Physiol.* 540: 139-152.

Oishi, K., Kawakita, E., and Uchida, M. K.: "Differentiation of neural stem cells into blood vessel cells and their modulators" (2002) *Nippon Yakurigaku Zasshi* (Japanese) 120 (1): 51P-53P.

Orkin, S.: "Embryonic stem cells and transgenic mice in the study of hematopoiesis". (1998) *Int. J. Dev. Biol.* 42:927-34.

Osborn, L., Hession, C., Tizard, R., Vassallo, C., Luhowskyj, S., Chi-Rosso, G., and Lobb, R.: "Direct expression cloning of vascular cell adhesion molecule 1, a cytokine-induced endothelial protein that binds to lymphocytes" (1989) *Cell* 59: 1203-11.

Partanen, J., Armstrong, E., Makela, T. P., Korhonen, J., Sandberg, M., Renkonen, R., Knuutila, S., Huebner, K., and Alitalo, K.: "A novel endothelial cell surface receptor tyrosine kinase with extracellular epidermal growth factor homology domains" (1992) *Mol. Cell. Biol.* 12: 1698-707.

Pesce, M. and Scholer, H. R.: "Oct-4: control of totipotency and germline determination" (2000) *Mol. Reprod. Dev.* 55: 452457.

Pittenger, M. F., Mackay, A. M., Beck, S. C., Jaiswal, R. K., Douglas, R., Mosca, J. D., Moorman, M. A., Simonetti, D. W., Craig, S., and Marshak, D. R.: "Multilineage potential of adult human MSCs". (1999) *Science* 284: 143-147

Pittenger, M., U.S. Pat. No. 5,827,740

Rajatska, A., Zarska, M., Quensel, C., and Krämer, J.: "Differentiation of the smooth muscle cell phenotypes during embryonic development of coronary vessels in the rat" (2001) *Histochem. Cell Biol.* 116: 79-87.

Reubinoff, B. E., Pera, M. F., Fong, C. Y., Trounson, A., and Bongso, A.: "ES cell lines from human blastocysts: somatic differentiation in vitro". (2000) *Nat Biotech* 18:399-404.

Ross, R.: "The smooth muscle cell. II. Growth of smooth muscle in culture and formation of elastic fibers" (1971) *J. Cell Biol.* 50(1): 172-86.

Ross, J. J. and R. T. Tranquillo. "ECM gene expression correlates with in vitro tissue growth and development in fibrin gel remodeled by neonatal smooth muscle cells," Matrix Biol 22:477-490 (2003).

Schwartz, et al., U.S. Pat. No. 5,759,793

Seliktar, D., Black, R. A. Vito, R. P. and Nerem, R. M.: "Dynamic mechanical conditioning of collagen-gel blood vessel constructs induces remodeling in vitro". (2000) *Ann. Biomed. Eng.* 28(4): 351-62.

Shamblott, M., Axelman, J., Wang, S., Bugg, E., Littlefield, J., Donovan, P., Blumenthal, P., Huggins, G., Gearhart, J.: "Derivation of pluripotent stem cells from cultured human primordial germ cells". (1998) *Proc. Natl. Acad. Sci. U.S.A.* 95: 13726-31.

Shi, Q., Rafli, S., Wu, M. H., Wijelath, E. S., Yu, C., Ishida, A., Fujita, Y., Kothari, S., Mohle, R., Sauvage, L. R., Moore, M. A., Storb, R. F., and Hammond, W. P.: "Evidence for circulating bone-marrow-derived endothelial cells" (1998) *Blood* 92: 362-7.

Shimizu, K., Sugiyama, S., Aikawa, M., Fukumoto, Y., Rabkin, E., Libby, P., and Mitchell, R. N.: "Host bone marrow cells are a source of donor intimal smooth muscle-like cells in murine aortic transplant arteriopathy." (2001) *Nat. Med.* 7: 738-741.

Shinoka, T., Shum-Tim, D., Ma, P. X., Tanel, R. E., Isogai, N., Langer, R., Vacanti, J. P., Mayer, J. E., Jr: "Creation of viable pulmonary artery autografts through tissue engineering". (1998) *J. Thoracic Cardiovasc. Surg.* 115(3): 536-45; discussion 545-6.

Shinoka, T., Imai, Y., and Ikada, Y.: "Transplantation of a tissue-engineered pulmonary artery" (2001) *N. Engl. J. Med.* 344(7): 532-3.

Simeone, A.: "Otx1 and Otx2 in the development and evolution of the mammalian brain" (1998) *EMBO J.* 117: 6790-8.

Simmons, P., et al., U.S. Pat. No. 5,677,136

Sobue, K., Hayashi, K., and Nishida, W.: "Expressional regulation of smooth muscle cell-specific genes in association with phenotypic modulation" (1999) *Mol. Cell Biochem.* 190 (1-2): 105-18.

Soule, H. D., Vazguez, J., Long, A., Albert, S., and Brennan, M.: "A human cell line from a pleural effusion derived from a breast carcinoma." (1973) *J. Natl. Cancer Inst.* 51(5): 1409-16

Stein, O., and Stein, Y.: "High-density lipoproteins reduce the uptake of low density lipoproteins by human endothelial cells in culture" (1976) *Biochim. Biophys. Acta* 431: 363-8.

Tao, Y. S., Edwards, R. A., Tubb, B., Wang, S., Bryan, J., McCrea, P. D.: "Beta-Catenin associates with the actin-bundling protein fascin in a noncadherin complex" (1996) *J. Cell Biol.* 134: 1271-81.

Thomson, J. A., Itskovitz-Eldor, J., Shapiro, S. S., Waknitz, M. A., Swiergiel, J. J., Marshall, V. S., and Jones, J. M.: "ES cell lines derived from human blastocysts". (1998) *Science* 282:114-7.

Thomson, J. A, Kalisman J., Golos, J., Durning, M., Harris, C., Becker, R., Hearn, J.: "Isolation of a primate embryonic stem cell line". (1995) *Proc. Natl. Acad. Sci. U.S.A.* 92: 7844-8.

Thomson, et al., U.S. Pat. No. 5,843,780

Thomson, et al., U.S. Pat. No. 6,200,806

Tsukamoto, et al., U.S. Pat. No. 5,750,397

Tsukamoto, et al., U.S. Pat. No. 5,716,827

Van Rijen, H., van Kempen, M. J., Analbers, L. J., Rook, M. B., van Ginneken, A. C., Gros, D., and Jongsma, H. J.: "Gap junctions in human umbilical cord endothelial cells contain multiple connexins" (1997) *Am. J. Physiol.* 272 (Pt. 1): C117-30.

Xu, C., Inokuma, M. S., Denham, J., Golds, K., Kundu, P., Gold, J. D., Carpenter, M. K.: "Feeder-free growth of undifferentiated human embryonic stem cells", (2001) *Nat. Biotech.* 19: 971.

Waltenberger, J., Claesson-Welsh, L., Siegbahn, A., Shibuya, M., and Heldin, C. H.: "Different signal transduction properties of KDR and Flt1, two receptors for vascular endothelial growth factor" (1994) *J. Biol. Chem.* 269: 26988-95.

Watson, P. M., Anderson, J. M., Vanltallie, C. M., and Doctrow, S. R.: "The tight-junction specific protein ZO-1 is a component of the human and rat blood-brain barriers" (1991) *Neurosci. Lett.* 129: 6-10.

Weinberg, C. B. and Bell, E.: "A blood vessel model constructed from collagen and cultured vascular cells" (1986) *Science* 231 (4736): 397-400.

Williams, R. L., Hilton, D. J., Pease, S., Willson, T. A., Stewart, C. If, Gearing, D. P., Wagner, E. F., Metcalf, D., Nicola, N. A., and Gough, N. M.: "Myeloid leukemia inhibitory factor maintains the developmental potential of ES cells". (1988) *Nature* 336: 684-7.

Wood, H. B. and Episkopou, V.: "Comparative expression of the mouse Sox1, Sox2 and Sox3 genes from pre-gastrulation to early somite stages" (1999) *Mech Dev.* 86(1-2): 197-201.

Won, Y. Y., David, H. T., and Bates, F. S.: "Giant Wormlike Rubber Micelles" (1999) *Science* 283: 960-963.

Yamashita, J. Itoh, H., Hirashima, M., Ogawa, M., Nishikawa, S., Yurugi, T., Naito, M., Nakao, K., and Nishikawa, S.: "Flk1-positive cells derived from embryonic stem cells serve as vascular progenitors" (2000) *Nature* 408: 92-96.

Yoo, J. U., Barthel, T. S., Nishimura, K., Solchaga, L., Caplan, A. I., Goldberg, V. M., Johnstone, B.: "The chondrogenic potential of human bone-marrow-derived mesenchymal progenitor cells". (1998) *J Bone Joint Surg Ain.* 12: 1745-57.

Young, H., et al., U.S. Pat. No. 5,827,735T

We claim:

1. A method of making an engineered blood vessel comprising an endothelial intimal layer surrounded by a smooth muscle medial layer, said method comprising contacting one or more factors with a matrix that is combined with endothelial cells and smooth muscle cells, wherein neither said endothelial cells combined with said matrix nor said smooth muscle cells combined with said matrix is exposed to said factors prior to combining both said endothelial cells and said smooth muscle cells with said matrix, said matrix that is combined with said endothelial cells and smooth muscle cells being circumferentially positioned around a tubular support, said factors being contained inside of said tubular support, wherein said support allows said one or more factors to move from the inside of said tubular support to said endothelial cells and smooth muscle cells in combination with said matrix, wherein said contacting results in the formation of said endothelial intimal layer surrounded by said smooth muscle medial layer, and wherein said one or more factors comprises:
    i) one or more mitogenic factors and one or more attractant factors; and/or
    ii) one or more mitoattractant factors.

2. The method of claim 1, wherein the endothelial cells are derived from stem cells.

3. The method of claim 2, wherein the stem cells are selected from the group consisting of embryonic stem cells, embryonic germ cells, non-embryonic cells that can form progeny of at least two germ layers, hematopoietic stem cells, mesenchymal stem cells, and endothelial progenitor cells.

4. The method of claim 2, wherein the stem cells are derived from bone marrow, brain, spinal cord, umbilical cord blood, liver, muscle, fat or placenta.

5. The method of claim 1, wherein the smooth muscle cells are derived from stem cells.

6. The method of claim 5, wherein the stem cells are selected from the group consisting of embryonic stem cells, embryonic germ cells, non-embryonic cells that can form progeny of at least two germ layers, mesenchymal stem cells, and smooth muscle progenitor cells.

7. The method of claim 1, wherein the matrix is comprised of a substance selected from the group consisting of fibrin, collagen, amphiphilic di-block copolymers, amphiphilic tri-block copolymers, and peptides.

8. The method of claim 1, wherein the support comprises porous plastic.

9. The method of claim 1, wherein the one or more mitoattractant factors is vascular endothelial growth factor.

10. A method of culturing cells in a matrix to produce an endothelial intimal layer surrounded by a smooth muscle medial layer, comprising the steps of:
    a) combining endothelial cells and smooth muscle cells with a matrix, wherein neither said endothelial cells nor said smooth muscle cells are cultured with said matrix prior to combining said endothelial cells and said smooth muscle cells with said matrix;
    b) growing said combination of endothelial cells, smooth muscle cells, and matrix on the exterior surface of a tubular support, wherein said tubular support allows movement of one or more factors within said tubular support to said combination of endothelial cells, smooth muscle cells, and matrix; and
    c) allowing movement of said one or more factors within said tubular support so as to contact, with said one or more factors, said combined endothelial cells and smooth muscle cells in said matrix, wherein said one or more factors are comprised of:
        i) one or more mitogenic factors and one or more attractant factors; and/or
        ii) one or more mitoattractant factors,
wherein said contact results in the formation of said endothelial intimal layer surrounded by said smooth muscle medial layer.

\* \* \* \* \*